(12) United States Patent
Forster et al.

(10) Patent No.: US 8,147,541 B2
(45) Date of Patent: Apr. 3, 2012

(54) METHODS AND DEVICES FOR DELIVERY OF PROSTHETIC HEART VALVES AND OTHER PROSTHETICS

(75) Inventors: David C. Forster, Menlo Park, CA (US); Scott Heneveld, Whitmore, CA (US); Brandon Walsh, Syracuse, UT (US); Brian Beckey, Woodside, CA (US)

(73) Assignee: AorTx, Inc., Redwood City, CA (US)

( * ) Notice: Subject to any disclaimer, the term of this patent is extended or adjusted under 35 U.S.C. 154(b) by 1030 days.

(21) Appl. No.: 11/363,961

(22) Filed: Feb. 27, 2006

(65) Prior Publication Data

US 2007/0203575 A1    Aug. 30, 2007

(51) Int. Cl.
A61F 2/24    (2006.01)
(52) U.S. Cl. ...................................... 623/2.11
(58) Field of Classification Search .............. 623/2.11, 623/1.11
See application file for complete search history.

(56) References Cited

U.S. PATENT DOCUMENTS

| | | |
|---|---|---|
| 376,531 A | 1/1888 | Byrnes |
| 1,314,601 A | 9/1919 | McCaskey |
| 3,579,642 A | 5/1971 | Hefferman |
| 3,587,115 A | 6/1971 | Shiley |
| 3,657,744 A | 4/1972 | Ersek |
| 3,671,979 A | 6/1972 | Moulopoulos |
| 3,755,823 A | 9/1973 | Hancock |
| 3,867,728 A | 2/1975 | Stubstad et al. |
| 4,056,854 A | 11/1977 | Boretos et al. |
| 4,106,129 A | 8/1978 | Carpentier et al. |
| 4,328,839 A | 5/1982 | Lyons et al. |
| 4,339,831 A | 7/1982 | Johnson |
| 4,340,091 A | 7/1982 | Skelton et al. |
| 4,624,822 A | 11/1986 | Arru et al. |
| 4,683,883 A | 8/1987 | Martin |
| 4,692,165 A | 9/1987 | Bokros |
| 4,758,151 A | 7/1988 | Arru et al. |
| 4,822,345 A | 4/1989 | Danforth |
| 4,822,353 A | 4/1989 | Bokros |
| 4,856,516 A | 8/1989 | Hillstead |
| 4,878,495 A * | 11/1989 | Grayzel ........................ 606/193 |
| 4,878,906 A | 11/1989 | Lindemann et al. |

(Continued)

FOREIGN PATENT DOCUMENTS

CN    200580012735.5    1/2009

(Continued)

OTHER PUBLICATIONS

U.S. Appl. No. 11/066,126—Office Action, Oct. 16, 2008.

(Continued)

*Primary Examiner* — Julian Woo
*Assistant Examiner* — Christopher L Templeton
(74) *Attorney, Agent, or Firm* — Dickstein Shapiro LLP; Mark Stirrat

(57) ABSTRACT

Prosthetic valves and their component parts are described, as are prosthetic valve delivery devices and methods for their use. The prosthetic valves are particularly adapted for use in percutaneous aortic valve replacement procedures. The delivery devices are particularly adapted for use in minimally invasive surgical procedures. The preferred delivery device includes a catheter having a deployment mechanism attached to its distal end, and a handle mechanism attached to its proximal end. A plurality of tethers are provided to selectively restrain the valve during deployment. A number of mechanisms for active deployment of partially expanded prosthetic valves are also described.

19 Claims, 36 Drawing Sheets

U.S. PATENT DOCUMENTS

| | | |
|---|---|---|
| 4,960,424 A | 10/1990 | Grooters |
| 4,994,077 A | 2/1991 | Dobben |
| 5,002,567 A | 3/1991 | Bona et al. |
| 5,037,434 A | 8/1991 | Lane |
| 5,078,737 A | 1/1992 | Bona et al. |
| 5,098,374 A | 3/1992 | Othel-Jacobsen et al. |
| 5,123,919 A | 6/1992 | Sauter et al. |
| 5,163,953 A | 11/1992 | Vince |
| 5,163,954 A | 11/1992 | Curcio et al. |
| 5,213,580 A | 5/1993 | Slepian et al. |
| 5,238,454 A | 8/1993 | Schmidt |
| 5,326,371 A | 7/1994 | Love et al. |
| 5,328,471 A | 7/1994 | Slepian |
| 5,370,685 A | 12/1994 | Stevens |
| 5,397,348 A | 3/1995 | Campbell et al. |
| 5,397,351 A | 3/1995 | Pavcnik et al. |
| 5,403,305 A | 4/1995 | Sauter et al. |
| 5,411,552 A | 5/1995 | Andersen et al. |
| 5,423,886 A | 6/1995 | Arru et al. |
| 5,443,474 A | 8/1995 | Sfakianos et al. |
| 5,454,838 A | 10/1995 | Vallana et al. |
| 5,522,885 A | 6/1996 | Love et al. |
| 5,531,094 A | 7/1996 | More et al. |
| 5,545,214 A | 8/1996 | Stevens |
| 5,554,185 A | 9/1996 | Block et al. |
| 5,560,487 A | 10/1996 | Starr |
| 5,582,607 A | 12/1996 | Lackman |
| 5,607,442 A | 3/1997 | Fischell et al. |
| 5,620,456 A | 4/1997 | Sauer et al. |
| 5,668,425 A | 9/1997 | Marioni et al. |
| 5,695,515 A | 12/1997 | Orejola |
| 5,713,860 A | 2/1998 | Kaplan et al. |
| 5,713,953 A | 2/1998 | Vallana et al. |
| 5,716,370 A | 2/1998 | Williamson, IV et al. |
| 5,724,705 A | 3/1998 | Hauser et al. |
| 5,772,672 A | 6/1998 | Toy et al. |
| 5,814,097 A | 9/1998 | Sterman et al. |
| 5,823,342 A | 10/1998 | Caudillo et al. |
| 5,840,081 A | 11/1998 | Andersen et al. |
| 5,855,601 A | 1/1999 | Bessler et al. |
| 5,868,708 A | 2/1999 | Hart et al. |
| 5,891,195 A | 4/1999 | Klostermeyer et al. |
| 5,919,225 A | 7/1999 | Lau et al. |
| 5,921,993 A | 7/1999 | Yoon |
| 5,925,063 A | 7/1999 | Khosravi |
| 5,957,949 A | 9/1999 | Leonhardt et al. |
| 5,980,570 A | 11/1999 | Simpson |
| 5,984,959 A | 11/1999 | Robertson et al. |
| 6,027,779 A | 2/2000 | Campbell et al. |
| 6,042,607 A | 3/2000 | Williamson, IV et al. |
| 6,051,014 A | 4/2000 | Jang |
| 6,053,922 A | 4/2000 | Krause et al. |
| 6,090,138 A | 7/2000 | Chasak et al. |
| 6,092,529 A | 7/2000 | Cox |
| 6,093,530 A | 7/2000 | McIlroy et al. |
| 6,102,944 A | 8/2000 | Huynh et al. |
| 6,102,945 A | 8/2000 | Campbell |
| 6,117,169 A | 9/2000 | Moe |
| 6,132,986 A | 10/2000 | Pathak et al. |
| 6,143,024 A | 11/2000 | Campbell et al. |
| 6,143,025 A | 11/2000 | Stobie et al. |
| 6,162,172 A | 12/2000 | Cosgrove et al. |
| 6,168,614 B1 | 1/2001 | Andersen et al. |
| 6,174,331 B1 | 1/2001 | Moe et al. |
| 6,182,664 B1 | 2/2001 | Cosgrove |
| 6,197,053 B1 | 3/2001 | Cosgrove et al. |
| 6,199,696 B1 | 3/2001 | Lytle et al. |
| 6,206,918 B1 | 3/2001 | Campbell et al. |
| 6,217,610 B1 | 4/2001 | Carpentier et al. |
| 6,231,578 B1 | 5/2001 | Rajhansa |
| 6,231,602 B1 | 5/2001 | Carpentier et al. |
| 6,241,765 B1 | 6/2001 | Briffin et al. |
| 6,245,102 B1 | 6/2001 | Jayaraman |
| 6,270,526 B1 | 8/2001 | Cox |
| 6,283,995 B1 | 9/2001 | Moe et al. |
| 6,287,339 B1 | 9/2001 | Vazquez et al. |
| 6,299,637 B1 | 10/2001 | Shaolian et al. |
| 6,299,638 B1 | 10/2001 | Sauter |
| 6,338,740 B1 | 1/2002 | Carpentier |
| 6,342,070 B1 | 1/2002 | Nguyen-Thien-Nhon |
| 6,348,068 B1 | 2/2002 | Campbell et al. |
| 6,350,281 B1 | 2/2002 | Rhee |
| 6,350,732 B1 | 2/2002 | Moore et al. |
| 6,364,905 B1 | 4/2002 | Simpson et al. |
| 6,371,983 B1 | 4/2002 | Lane |
| 6,383,147 B1 | 5/2002 | Stobie |
| 6,391,054 B2 | 5/2002 | Carpentier et al. |
| 6,402,780 B2 | 6/2002 | Williamson, IV et al. |
| 6,405,084 B2 | 6/2002 | Plicchi et al. |
| 6,409,758 B2 | 6/2002 | Stobie et al. |
| 6,425,916 B1 | 7/2002 | Garrison et al. |
| 6,453,062 B1 | 9/2002 | MacNutt et al. |
| 6,454,799 B1 | 9/2002 | Schreck |
| 6,458,155 B1 | 10/2002 | Van Nguyen et al. |
| 6,461,382 B1 | 10/2002 | Cao |
| 6,475,239 B1 | 11/2002 | Campbell et al. |
| 6,479,079 B1 | 11/2002 | Pathak et al. |
| 6,482,228 B1 | 11/2002 | Norred |
| 6,485,512 B1 | 11/2002 | Cheng |
| 6,493,585 B2 | 12/2002 | Plicchi et al. |
| 6,530,952 B2 | 3/2003 | Vesely |
| 6,544,279 B1 | 4/2003 | Hopkins et al. |
| 6,558,418 B2 | 5/2003 | Carpentier et al. |
| 6,565,602 B2 | 5/2003 | Rolando et al. |
| 6,569,196 B1 | 5/2003 | Vesely |
| 6,572,642 B2 | 6/2003 | Rinaldi et al. |
| 6,582,462 B1 | 6/2003 | Andersen et al. |
| 6,585,632 B2 | 7/2003 | Vallana et al. |
| 6,585,766 B1 | 7/2003 | Huynh et al. |
| 6,596,471 B2 | 7/2003 | Pathak et al. |
| 6,602,288 B1 | 8/2003 | Cosgrove et al. |
| 6,613,085 B1 | 9/2003 | Anderson et al. |
| 6,616,690 B2 | 9/2003 | Rolando et al. |
| 6,635,085 B1 | 10/2003 | Caffey et al. |
| 6,638,303 B1 | 10/2003 | Campbell |
| 6,652,578 B2 | 11/2003 | Bailey et al. |
| 6,663,667 B2 | 12/2003 | Dehdashtian et al. |
| 6,673,109 B2 | 1/2004 | Cox |
| 6,679,871 B2 | 1/2004 | Hahnen |
| 6,682,543 B2 | 1/2004 | Barbut et al. |
| 6,682,558 B2 | 1/2004 | Tu et al. |
| 6,682,559 B2 | 1/2004 | Myers et al. |
| 6,689,149 B2 | 2/2004 | Maahs |
| 6,692,512 B2 | 2/2004 | Jang |
| 6,706,033 B1 | 3/2004 | Martinez et al. |
| 6,719,787 B2 | 4/2004 | Cox |
| 6,719,788 B2 | 4/2004 | Cox |
| 6,719,789 B2 | 4/2004 | Cox |
| 6,723,122 B2 | 4/2004 | Yang et al. |
| 6,730,118 B2 | 5/2004 | Spenser et al. |
| 6,733,513 B2 | 5/2004 | Boyle et al. |
| 6,733,525 B2 | 5/2004 | Yang et al. |
| 6,736,845 B2 | 5/2004 | Marquez et al. |
| 6,736,846 B2 | 5/2004 | Cox |
| 6,767,362 B2 | 7/2004 | Schreck |
| 6,770,083 B2 | 8/2004 | Seguin |
| 6,783,988 B1 | 8/2004 | Dinh et al. |
| 6,790,219 B1 | 9/2004 | Murphy |
| 6,796,972 B1 | 9/2004 | Sinofsky et al. |
| 6,797,000 B2 | 9/2004 | Simpson et al. |
| 6,805,710 B2 | 10/2004 | Bolling et al. |
| 6,821,279 B2 | 11/2004 | Di Emidio |
| 6,821,297 B2 | 11/2004 | Snyders |
| 6,846,324 B2 | 1/2005 | Stobie |
| 6,849,088 B2 | 2/2005 | Dehdashtian et al. |
| 6,858,039 B2 | 2/2005 | McCarthy |
| 6,875,231 B2 | 4/2005 | Anduiza et al. |
| 6,878,168 B2 | 4/2005 | Carpentier et al. |
| 6,893,460 B2 | 5/2005 | Spenser et al. |
| 6,896,698 B2 | 5/2005 | Rolando et al. |
| 6,908,481 B2 | 6/2005 | Cribier |
| 6,939,365 B1 | 9/2005 | Fogarty et al. |
| 6,945,997 B2 | 9/2005 | Huynh et al. |
| 6,951,571 B1 | 10/2005 | Srivastava |
| 6,962,605 B2 | 11/2005 | Cosgrove et al. |
| 6,986,775 B2 | 1/2006 | Morales et al. |
| 6,988,881 B2 | 1/2006 | Motsenbocker et al. |

| | | |
|---|---|---|
| 6,989,028 B2 | 1/2006 | Lashinski et al. |
| 7,004,176 B2 | 2/2006 | Lau |
| 7,011,669 B2 | 3/2006 | Kimblad |
| 7,011,681 B2 | 3/2006 | Vesely |
| 7,011,682 B2 | 3/2006 | Lashinski et al. |
| 7,014,648 B2 | 3/2006 | Ambrisco et al. |
| 7,018,406 B2 | 3/2006 | Seguin et al. |
| 7,060,092 B2 | 6/2006 | Kuribayashi et al. |
| 7,252,682 B2 | 8/2007 | Seguin |
| 7,374,571 B2 | 5/2008 | Pease et al. |
| 7,429,270 B2 | 9/2008 | Baumgartner et al. |
| 2001/0016758 A1 | 8/2001 | Plicchi et al. |
| 2001/0018600 A1 | 8/2001 | Plicchi et al. |
| 2001/0039450 A1 | 11/2001 | Pavcnik et al. |
| 2001/0049541 A1 | 12/2001 | Plicchi et al. |
| 2001/0053929 A1* | 12/2001 | Vonesh et al. ............... 623/1.12 |
| 2002/0032482 A1 | 3/2002 | Cox |
| 2002/0038128 A1 | 3/2002 | Turovkiy et al. |
| 2002/0042651 A1 | 4/2002 | Liddicoat et al. |
| 2002/0052647 A1 | 5/2002 | Rolando et al. |
| 2002/0055775 A1 | 5/2002 | Carpentier et al. |
| 2002/0058994 A1 | 5/2002 | Hill et al. |
| 2002/0072793 A1 | 6/2002 | Rolando et al. |
| 2002/0095173 A1 | 7/2002 | Mazzocchi et al. |
| 2002/0099441 A1 | 7/2002 | Dehdashtian |
| 2002/0117264 A1 | 8/2002 | Rinaldi et al. |
| 2002/0133226 A1 | 9/2002 | Marquez et al. |
| 2002/0138138 A1 | 9/2002 | Yang |
| 2002/0161431 A1 | 10/2002 | Stobie et al. |
| 2002/0163104 A1 | 11/2002 | Motsenbocker et al. |
| 2002/0183766 A1 | 12/2002 | Seguin |
| 2002/0183831 A1 | 12/2002 | Rolando et al. |
| 2003/0009076 A1 | 1/2003 | Vallana et al. |
| 2003/0023262 A1 | 1/2003 | Welch |
| 2003/0027332 A1 | 2/2003 | Lafrance et al. |
| 2003/0033002 A1 | 2/2003 | Dehdashtian et al. |
| 2003/0036795 A1 | 2/2003 | Andersen et al. |
| 2003/0050694 A1 | 3/2003 | Yang et al. |
| 2003/0055495 A1 | 3/2003 | Pease et al. |
| 2003/0065356 A1 | 4/2003 | Tsugita et al. |
| 2003/0114913 A1 | 6/2003 | Spenser et al. |
| 2003/0114917 A1 | 6/2003 | Holloway et al. |
| 2003/0130721 A1 | 7/2003 | Martin et al. |
| 2003/0153943 A1 | 8/2003 | Michael et al. |
| 2003/0153946 A1 | 8/2003 | Kimblad |
| 2003/0195613 A1 | 10/2003 | Curcio et al. |
| 2003/0212433 A1 | 11/2003 | Ambrisco et al. |
| 2004/0015224 A1 | 1/2004 | Armstrong et al. |
| 2004/0030382 A1 | 2/2004 | St. Goar et al. |
| 2004/0034380 A1 | 2/2004 | Woolfson et al. |
| 2004/0049266 A1 | 3/2004 | Anduiza et al. |
| 2004/0078074 A1 | 4/2004 | Anderson et al. |
| 2004/0087965 A1* | 5/2004 | Levine et al. ............... 606/108 |
| 2004/0092858 A1 | 5/2004 | Wilson et al. |
| 2004/0092989 A1 | 5/2004 | Wilson et al. |
| 2004/0093060 A1 | 5/2004 | Seguin et al. |
| 2004/0093080 A1 | 5/2004 | Helmus et al. |
| 2004/0127979 A1 | 7/2004 | Wilson et al. |
| 2004/0148017 A1 | 7/2004 | Stobie |
| 2004/0148018 A1 | 7/2004 | Carpentier et al. |
| 2004/0153140 A1 | 8/2004 | Rolando et al. |
| 2004/0158276 A1 | 8/2004 | Barbut et al. |
| 2004/0172124 A1 | 9/2004 | Vallana et al. |
| 2004/0186563 A1 | 9/2004 | Lobbi |
| 2004/0199245 A1 | 10/2004 | Lauterjung |
| 2004/0210304 A1 | 10/2004 | Seguin et al. |
| 2004/0225352 A1 | 11/2004 | Osborne et al. |
| 2004/0243222 A1 | 12/2004 | Osborne et al. |
| 2004/0249433 A1 | 12/2004 | Freitag |
| 2005/0027337 A1 | 2/2005 | Rudko et al. |
| 2005/0033398 A1 | 2/2005 | Seguin |
| 2005/0038497 A1 | 2/2005 | Neuendorf et al. |
| 2005/0043760 A1 | 2/2005 | Fogarty et al. |
| 2005/0043790 A1 | 2/2005 | Seguin |
| 2005/0043792 A1 | 2/2005 | Solem et al. |
| 2005/0065594 A1 | 3/2005 | DiMatteo et al. |
| 2005/0075584 A1 | 4/2005 | Cali |
| 2005/0075712 A1 | 4/2005 | Biancucci et al. |
| 2005/0075725 A1 | 4/2005 | Rowe |
| 2005/0090888 A1 | 4/2005 | Hines et al. |
| 2005/0096734 A1 | 5/2005 | Majercak et al. |
| 2005/0096740 A1 | 5/2005 | Langberg et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0228485 A1 | 10/2005 | Rolando et al. |
| 2005/0228495 A1 | 10/2005 | Macoviak |
| 2005/0267493 A1 | 12/2005 | Schreck et al. |
| 2005/0277959 A1 | 12/2005 | Cosgrove et al. |
| 2005/0288764 A1* | 12/2005 | Snow et al. ............... 623/1.11 |
| 2006/0004442 A1 | 1/2006 | Spenser et al. |
| 2006/0015179 A1 | 1/2006 | Bulman-Fleming et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0052867 A1 | 3/2006 | Revuelta |
| 2006/0058871 A1 | 3/2006 | Zakay et al. |
| 2006/0069424 A1* | 3/2006 | Acosta et al. ............... 623/1.12 |
| 2006/0095052 A1 | 5/2006 | Chambers |
| 2006/0122633 A1 | 6/2006 | To et al. |
| 2006/0173537 A1 | 8/2006 | Yang et al. |
| 2006/0217764 A1 | 9/2006 | Abbott et al. |
| 2007/0016281 A1* | 1/2007 | Melsheimer ............... 623/1.11 |
| 2007/0016286 A1 | 1/2007 | Herrmann et al. |
| 2007/0088431 A1 | 4/2007 | Bourang et al. |
| 2008/0140172 A1 | 6/2008 | Carpenter et al. |

FOREIGN PATENT DOCUMENTS

| | | |
|---|---|---|
| CN | 200580012735.5 | 7/2009 |
| EP | 05723873.5 | 11/2009 |
| WO | WO 91/17730 | 11/1991 |
| WO | WO 99/33414 | 7/1999 |
| WO | WO 01/76510 A2 | 10/2001 |
| WO | WO 03/003949 A2 | 1/2003 |
| WO | WO 03/047468 A1 | 6/2003 |
| WO | WO 03/096932 A1 | 11/2003 |
| WO | WO 03/105670 A2 | 12/2003 |
| WO | WO 2005009285 A2 | 2/2005 |
| WO | WO 2005/076973 A2 | 8/2005 |
| WO | WO 2005/087140 A1 | 9/2005 |
| WO | WO 2006/066150 A2 | 6/2006 |
| WO | WO2007/101160 | 12/2007 |
| WO | WO2007/149910 | 1/2008 |
| WO | WO2008/030946 | 1/2008 |
| WO | WO2007/101159 | 4/2008 |
| WO | WO2007/149841 | 7/2008 |
| WO | WO2007/149905 | 8/2008 |
| WO | WO2007/149933 | 8/2008 |

OTHER PUBLICATIONS

U.S. Appl. No. 11/066,126—Office Action, Apr. 3, 2009.
U.S. Appl. No. 11/066,126—Office Action, Dec. 22, 2009.
U.S. Appl. No. 11/066,124—Office Action, Mar. 7, 2007.
U.S. Appl. No. 11/066,124—Office Action, Mar. 7, 2008.
U.S. Appl. No. 11/066,124—Office Action, Oct. 2, 2008.
U.S. Appl. No. 11/066,124—Office Action, Jun. 9, 2009.
U.S. Appl. No. 11/067,330—Office Action, Apr. 16, 2007.
U.S. Appl. No. 11/067,330—Office Action, Jun. 11, 2008.
U.S. Appl. No. 11/067,330—Office Action, Jun. 10, 2009.
U.S. Appl. No. 11/364,715—Office Action, Dec. 11, 2006.
U.S. Appl. No. 11/364,715—Office Action, Oct. 18, 2007.
U.S. Appl. No. 11/364,715—Office Action, Jan. 12, 2009.
European Search Report, Appln. No. 07798835.0-2320, Mar. 2, 2010.

European Search Report, Appln. No. 07814708.9-2320, Mar. 3, 2010.
European Search Report, Appln. No. 07798811.2-2320, Mar. 8, 2010.
European Search Report, Appln. No. 07757493.7-2320, Mar. 15, 2010.

* cited by examiner

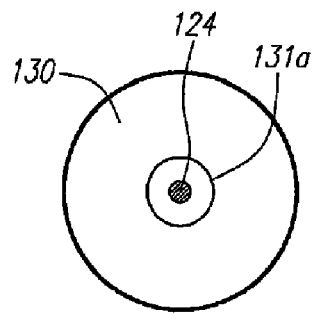
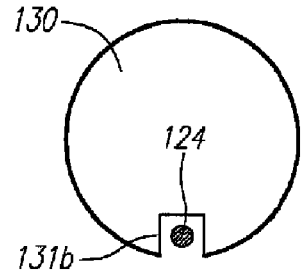
FIG. 3D          FIG. 3E
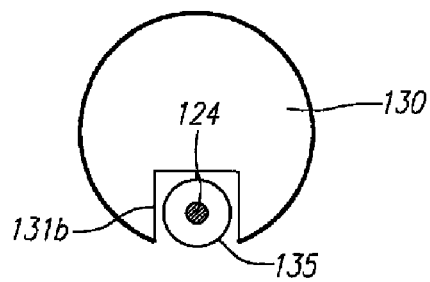
FIG. 3F
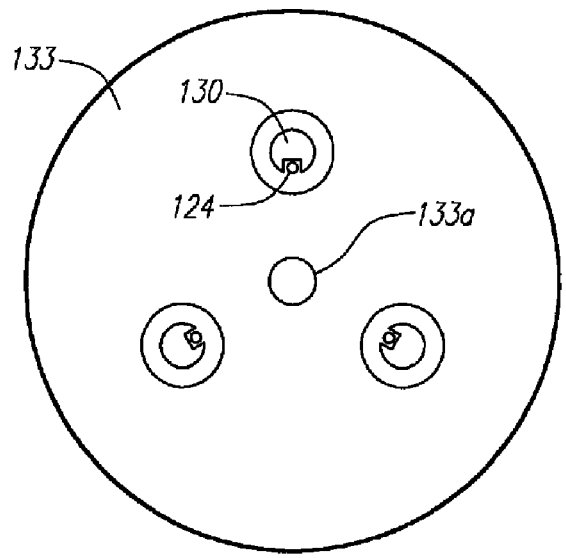
FIG. 3G

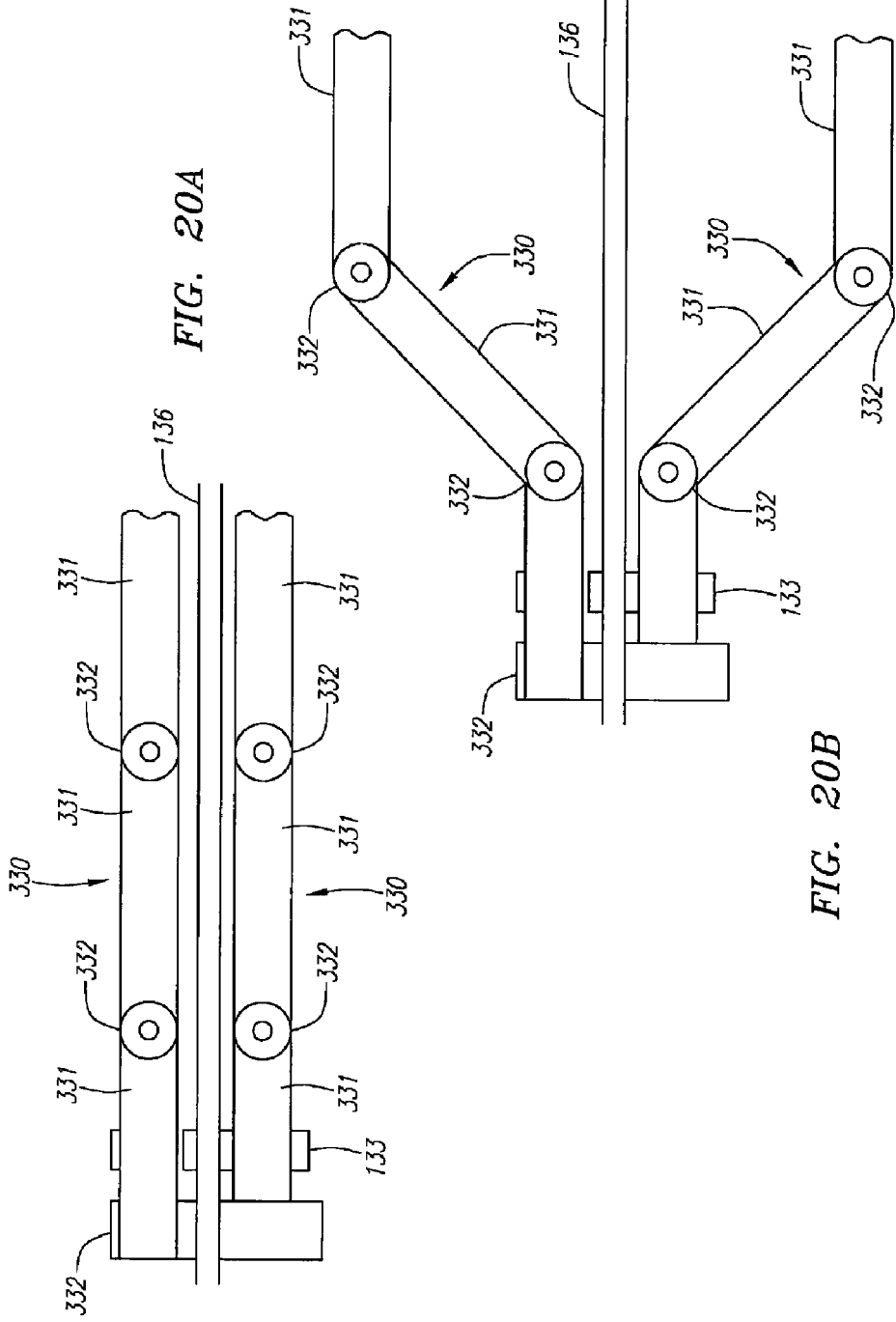

METHODS AND DEVICES FOR DELIVERY OF PROSTHETIC HEART VALVES AND OTHER PROSTHETICS

CROSS REFERENCES TO RELATED APPLICATIONS

This application relates to U.S. patent application Ser. No. 11/066,126, entitled "Prosthetic Heart Valves, Scaffolding Structures, and Methods for Implantation of Same," filed Feb. 25, 2005, which application is hereby incorporated by reference in its entirety. The foregoing application claims the benefit of U.S. Provisional Application Ser. No. 60/548,731, entitled "Foldable Stent for Minimally Invasive Surgery," filed Feb. 27, 2004, and U.S. Provisional Application Ser. No. 60/559,199, entitled "Method and Multiple Balloon for Percutaneous Aortic Valve Implantation," filed Apr. 1, 2004, each of which applications is hereby incorporated by reference in its entirety.

FIELD OF THE INVENTION

The present invention relates generally to medical devices and methods. More particularly, the present invention relates to methods and devices for delivering and deploying prosthetic heart valves and similar structures using minimally invasive surgical methods.

BACKGROUND OF THE INVENTION

Diseases and other disorders of the heart valve affect the proper flow of blood from the heart. Two categories of heart valve disease are stenosis and incompetence. Stenosis refers to a failure of the valve to open fully, due to stiffened valve tissue. Incompetence refers to valves that cause inefficient blood circulation by permitting backflow of blood in the heart.

Medication may be used to treat some heart valve disorders, but many cases require replacement of the native valve with a prosthetic heart valve. Prosthetic heart valves can be used to replace any of the native heart valves (aortic, mitral, tricuspid or pulmonary), although repair or replacement of the aortic or mitral valves is most common because they reside in the left side of the heart where pressures are the greatest. Two primary types of prosthetic heart valves are commonly used, mechanical heart valves and prosthetic tissue heart valves.

The caged ball design is one of the early mechanical heart valves. The caged ball design uses a small ball that is held in place by a welded metal cage. In the mid-1960s, another prosthetic valve was designed that used a tilting disc to better mimic the natural patterns of blood flow. The tilting-disc valves had a polymer disc held in place by two welded struts. The bileaflet valve was introduced in the late 1970s. It included two semicircular leaflets that pivot on hinges. The leaflets swing open completely, parallel to the direction of the blood flow. They do not close completely, which allows some backflow.

The main advantages of mechanical valves are their high durability. Mechanical heart valves are placed in young patients because they typically last for the lifetime of the patient. The main problem with all mechanical valves is the increased risk of blood clotting.

Prosthetic tissue valves include human tissue valves and animal tissue valves. Both types are often referred to as bioprosthetic valves. The design of bioprosthetic valves are closer to the design of the natural valve. Bioprosthetic valves do not require long-term anticoagulants, have better hemodynamics, do not cause damage to blood cells, and do not suffer from many of the structural problems experienced by the mechanical heart valves.

Human tissue valves include homografts, which are valves that are transplanted from another human being, and autografts, which are valves that are transplanted from one position to another within the same person.

Animal tissue valves are most often heart tissues recovered from animals. The recovered tissues are typically stiffened by a tanning solution, most often glutaraldehyde. The most commonly used animal tissues are porcine, bovine, and equine pericardial tissue.

The animal tissue valves are typically stented valves. Stentless valves are made by removing the entire aortic root and adjacent aorta as a block, usually from a pig. The coronary arteries are tied off, and the entire section is trimmed and then implanted into the patient.

A conventional heart valve replacement surgery involves accessing the heart in the patent's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

A less invasive approach to valve replacement is desired. The percutaneous implantation of a prosthetic valve is a preferred procedure because the operation is performed under local anesthesia, does not require cardiopulmonary bypass, and is less traumatic. Current attempts to provide such a device generally involve stent-like structures, which are very similar to those used in vascular stent procedures with the exception of being larger diameter as required for the aortic anatomy, as well as having leaflets attached to provide one way blood flow. These stent structures are radially contracted for delivery to the intended site, and then expanded/deployed to achieve a tubular structure in the annulus. The stent structure needs to provide two primary functions. First, the structure needs to provide adequate radial stiffness when in the expanded state. Radial stiffness is required to maintain the cylindrical shape of the structure, which assures the leaflets coapt properly. Proper leaflet coaption assures the edges of the leaflets mate properly, which is necessary for proper sealing without leaks. Radial stiffness also assures that there will be no paravalvular leakage, which is leaking between the valve and aorta interface, rather than through the leaflets. An additional need for radial stiffness is to provide sufficient interaction between the valve and native aortic wall that there will be no valve migration as the valve closes and holds full body blood pressure. This is a requirement that other vascular devices are not subjected to. The second primary function of the stent structure is the ability to be crimped to a reduced size for implantation.

Prior devices have utilized traditional stenting designs which are produced from tubing or wire wound structures. Although this type of design can provide for crimpability, it provides little radial stiffness. These devices are subject to "radial recoil" in that when the device is deployed, typically with balloon expansion, the final deployed diameter is smaller than the diameter the balloon and stent structure were expanded to. The recoil is due in part because of the stiffness mismatches between the device and the anatomical environment in which it is placed. These devices also commonly cause crushing, tearing, or other deformation to the valve leaflets during the contraction and expansion procedures. Other stenting designs have included spirally wound metallic sheets. This type of design provides high radial stiffness, yet crimping results in large material strains that can cause stress fractures and extremely large amounts of stored energy in the constrained state. Replacement heart valves are expected to survive for many years when implanted. A heart valve sees approximately 500,000,000 cycles over the course of 15 years. High stress states during crimping can reduce the fatigue life of the device. Still other devices have included tubing, wire wound structures, or spirally wound sheets formed of nitinol or other superelastic or shape memory material. These devices suffer from some of the same deficiencies as those described above.

A number of improved prosthetic heart valves and scaffolding structures are described in co-pending U.S. patent application Ser. No. 11/066,126, entitled "Prosthetic Heart Valves, Scaffolding Structures, and Methods for Implantation of Same," filed Feb. 25, 2005, ("the '126 application") which application is hereby incorporated by reference in its entirety. Several of the prosthetic heart valves described in the '126 application include a support member having a valvular body attached, the support member preferably comprising a structure having three panels separated by three foldable junctions. The '126 application also describes several delivery mechanisms adapted to deliver the described prosthetic heart valve. Although the prosthetic heart valves and delivery systems described in the '126 application represent a substantial advance in the art, additional delivery systems and methods are desired, particularly such systems and methods that are adapted to deliver and deploy the prosthetic heart valves described therein.

SUMMARY OF THE INVENTION

The present invention provides methods and devices for deploying prosthetic heart valves and other prosthetic devices in body lumens. The methods and devices are particularly adapted for use in percutaneous aortic valve replacement. The methods and devices may also find use in the peripheral vasculature, the abdominal vasculature, and in other ducts such as the biliary duct, the fallopian tubes, and similar lumen structures within the body of a patient. Although particularly adapted for use in lumens found in the human body, the apparatus and methods may also find application in the treatment of animals.

Without intending to limit the scope of the methods and devices described herein, the deployment devices and methods are particularly adapted for delivery of prosthetic heart valves and scaffolding structures identical or similar to those described in the '126 application described above. A particularly preferred prosthetic heart valve includes a generally cylindrical support structure formed of three segments, such as panels, interconnected by three foldable junctions, such as hinges, a representative embodiment of which is illustrated in FIG. 1A of the '126 application, which is reproduced herein as FIG. 1A. The exemplary prosthetic valve 30 includes a generally cylindrical support member 32 made up of three generally identical curved panels 36 and a valvular body 34 attached to the internal surface of the support member. Each panel includes an aperture 40 through which extends a plurality of interconnecting braces 42 that define a number of sub-apertures 44, 46, 48, 50. A hinge 52 is formed at the junction formed between each pair of adjacent panels. The hinge may be a membrane hinge comprising a thin sheet of elastomeric material 54 attached to the external edge 56 of each of a pair of adjacent panels 36.

Turning to FIG. 1B-C, a method for transforming a prosthetic valve from its expanded state to its contracted state is illustrated. These Figures show a three-panel support member without a valvular body attached. The method for contracting a full prosthetic valve, including the attached valvular body, is similar to that described herein in relation to the support member alone. As shown in FIG. 1B, each of the panels 36 is first inverted, by which is meant that a longitudinal centerline 80 of each of the panels 36 is forced radially inward toward the central longitudinal axis 82 of the support member. This action is facilitated by having panels formed of a thin, resilient sheet of material having generally elastic properties, and by the presence of the hinges 52 located at the junction between each pair of adjacent panels 36. During the inversion step, the edges 56 of each of the adjacent pairs of panels fold upon one another at the hinge 52. The resulting structure, shown in FIG. 1B, is a three-vertex 58 star shaped structure, referred to herein as a "tri-star" shape. Those skilled in the art will recognize that a similar procedure may be used to invert a four (or more) panel support member, in which case the resulting structure would be a four- (or more) vertex star shaped structure.

The prosthetic valve 30 may be further contracted by curling each of the vertices 58 of the star shaped structure to form a multi-lobe structure, as shown in FIG. 1C. As shown in that Figure, each of the three vertices 58 is rotated toward the center longitudinal axis 82 of the device, causing each of the three folded-upon edges of the adjacent pairs of panels to curl into a lobe 84. The resulting structure, illustrated in FIG. 1C, is a "tri-lobe" structure that represents the fully contracted state of the prosthetic valve. Those skilled in the art will recognize that a similar procedure may be used to fully contract a four (or more) panel support member, in which case the resulting structure would be a four- (or more) lobed structure.

The foregoing processes are performed in reverse to transform the prosthetic valve from its contracted state to its expanded state. For example, beginning with the prosthetic valve in its "tri-lobe" position shown in FIG. 1C, the three vertices 58 may be extended radially to achieve the "tri-star" shape shown in FIG. 1B. The "tri-star" shape shown in FIG. 1B is typically not stable, as the panels 36 tend to spontaneously expand from the inverted shape to the fully expanded shape shown in FIG. 1A unless the panels are otherwise constrained. Alternatively, if the panels do not spontaneously transition to the expanded state, it will typically only require a slight amount of force over a relatively short amount of distance in order to cause the panels to fully expand. For example, because of the geometry of the three panel structure, a structure having an expanded diameter of about 21 mm would be fully expanded by insertion of an expanding member having a diameter of only 16 mm into the interior of the structure. In such a circumstance, the 16 mm diameter member would contact the centerline of each panel and provide sufficient force to cause each panel to transform from the inverted shape shown in FIG. 1B to the fully expanded shape shown in FIG. 1A. This is in contrast to a typical "stent"-like support structure, which requires an expanding member to expand the stent to its full radial distance.

Additional details of this and other embodiments of the prosthetic heart valve and scaffolding structures are provided in the '126 application, to which the present description refers. It is to be understood that those prosthetic heart valves and scaffolding structures are only examples of such valves and prosthetic devices that are suitable for use with the devices and methods described herein. For example, the present devices and methods are suitable for delivering valves and prosthetic devices having any cross-sectional or longitudinal profile, and is not limited to those valves and devices described in the '126 application or elsewhere.

Turning to the deployment devices and methods, in one aspect of the present invention, a delivery catheter for prosthetic heart valves and other devices is provided. The delivery catheter is preferably adapted for use with a conventional guidewire, having an internal longitudinal lumen for passage of the guidewire. The delivery catheter includes a handle portion located at a proximal end of the catheter, a deployment mechanism located at the distal end of the catheter, and a catheter shaft interposed between and operatively interconnecting the handle portion and the deployment mechanism. The deployment mechanism includes several components that provide the delivery catheter with the ability to receive and retain a prosthetic valve or other device in a contracted, delivery state, to convert the prosthetic device to a partially expanded state, and then to release the prosthetic valve completely from the delivery device. In several preferred embodiments, the deployment mechanism includes an outer slotted tube, a plurality of wrapping pins attached to a hub and located on the interior of the slotted tube, and a plurality of restraining members that extend through the wrapping pins to the distal end of the catheter. Each of the deployment mechanism components is individually controlled by a corresponding mechanism carried on the handle portion of the catheter. The deployment mechanism preferably also includes a nosecone having an atraumatic distal end.

In several particularly preferred embodiments, the restraining members comprise tethers in the form of a wire, a cable, or other long, thin member made up of one or more of a metal such as stainless steel, metallic alloys, polymeric materials, or other suitable materials. A particularly preferred form of the tethers is suture material. In several embodiments, the tethers are adapted to engage the guidewire that extends distally past the distal end of the delivery catheter. The tethers preferably engage the guidewire by having a loop, an eyelet, or other similar construction at the distal end of the tether. Optionally, the tether is simply looped around the guidewire and doubles back to the catheter handle. Thus, the tethers are released when the guidewire is retracted proximally into the delivery catheter. In still other embodiments, the tethers may be released from the guidewire by actuation of a member carried on the handle mechanism at the proximal end of the catheter. In still other embodiments, a post or tab is provided on the guidewire, and the tether engages the post or tab but is able to bend or break free from the post or tab when a proximally-oriented force is applied to the tethers.

In a second aspect of the present invention, several optional active deployment mechanisms are described. The active deployment mechanisms are intended to convert a prosthetic valve, scaffolding structure, or similar device from an undeployed, partially deployed, or not-fully deployed state to its fully expanded state. Several of the active deployment mechanisms take advantage of the fact that the preferred prosthetic valves and scaffolding structures require only a small amount of force applied to any of a large number of points or locations on the valve or structure in order to cause the valve to fully expand. Exemplary embodiments of the active deployment mechanisms include embodiments utilizing expandable members that are placed into the interior of the prosthetic valve and then expanded; embodiments that operate by causing the hinges of the undeployed prosthetic valve to open, thereby transitioning to the fully expanded state; embodiments that include implements that engage one or more of the panels to cause the panel to expand to its deployed state; and other embodiments described herein.

Other aspects, features, and functions of the inventions described herein will become apparent by reference to the drawings and the detailed description of the preferred embodiments set forth below.

DESCRIPTION OF THE DRAWINGS

FIGS. 3D-F are cross-sectional views of wrapping pins and their associated tethers.

FIG. 3G is another perspective view of a wrapping pin stabilizer.

FIG. 9A is a closeup view of the nosecone and guidewire shown in FIG. 9, showing detail of the manner in which a tether is looped over the guidewire.

FIG. 14A shows a valve in its expanded state, and FIG. 14B shows the valve in its "tri-star" state.

FIGS. 20A-B are side views in partial cross-section showing a pair (out of three) of articulating wrapping pins, forming a gripper mechanism.

DETAILED DESCRIPTION OF THE PREFERRED EMBODIMENTS

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present inventions.

A. Delivery Devices and Methods of Use

Figure 2:
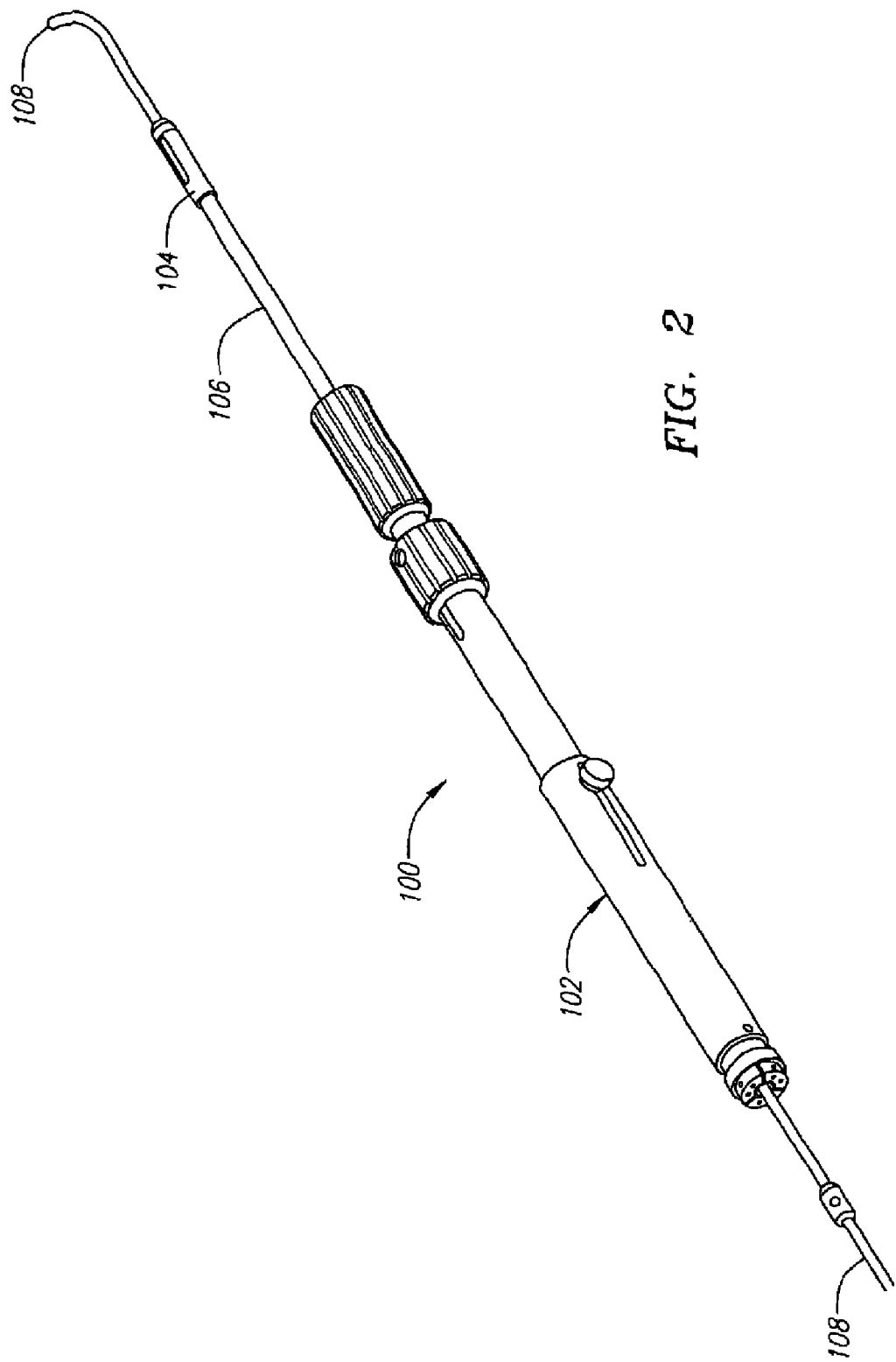
FIG. 2 is a perspective view of a delivery catheter in accordance with the present invention.

Devices for delivering prosthetic valves and other devices to a treatment location in a body lumen are described below, as are methods for their use. The delivery devices are particularly adapted for use in minimally invasive interventional procedures, such as percutaneous aortic valve replacements. FIG. 2 illustrates a preferred embodiment of the device, in the form of a delivery catheter. The delivery catheter 100 includes a handle mechanism 102 located at the proximal end of the catheter, a deployment mechanism 104 located at the distal end of the device, and a shaft 106 extending between and interconnecting the handle mechanism 102 and the deployment mechanism 104. The catheter 100 is preferably provided with a guidewire lumen extending through the entire length of the catheter, such that a guidewire 108 is able to extend through the delivery catheter in an "over-the-wire" construction. In an optional embodiment (not shown in the drawings), the catheter 100 is provided with a "rapid-exchange" construction whereby the guidewire exits the catheter shaft through an exit port located near the distal end of the catheter. The cross-sectional profile of the deployment mechanism 104 and the shaft 106 are of a sufficiently small size that they are able to be advanced within the vasculature of a patient to a target location, such as the valve root of one or more of the valves of the heart. A preferred route of entry is through the femoral artery in a manner known to those skilled in the art. Thus, the deployment mechanism 104 has a preferred maximum diameter of approximately 24 Fr. It is understood, however, that the maximum and minimum transverse dimensions of the deployment mechanism 104 may be varied in order to obtain necessary or desired results.

The deployment mechanism 104 is provided with components, structures, and/or features that provide the delivery catheter with the ability to retain a prosthetic valve (or other prosthetic device) in a contracted state, to deliver the valve to a treatment location, to convert the prosthetic valve to its deployed state (or to allow the valve to convert to its deployed state on its own), to retain control over the valve to make any necessary final position adjustments, and to convert the prosthetic valve to its contracted state and withdraw the valve (if needed). These components, structures, and/or features of the preferred deployment mechanism are described below.

Figure 3:
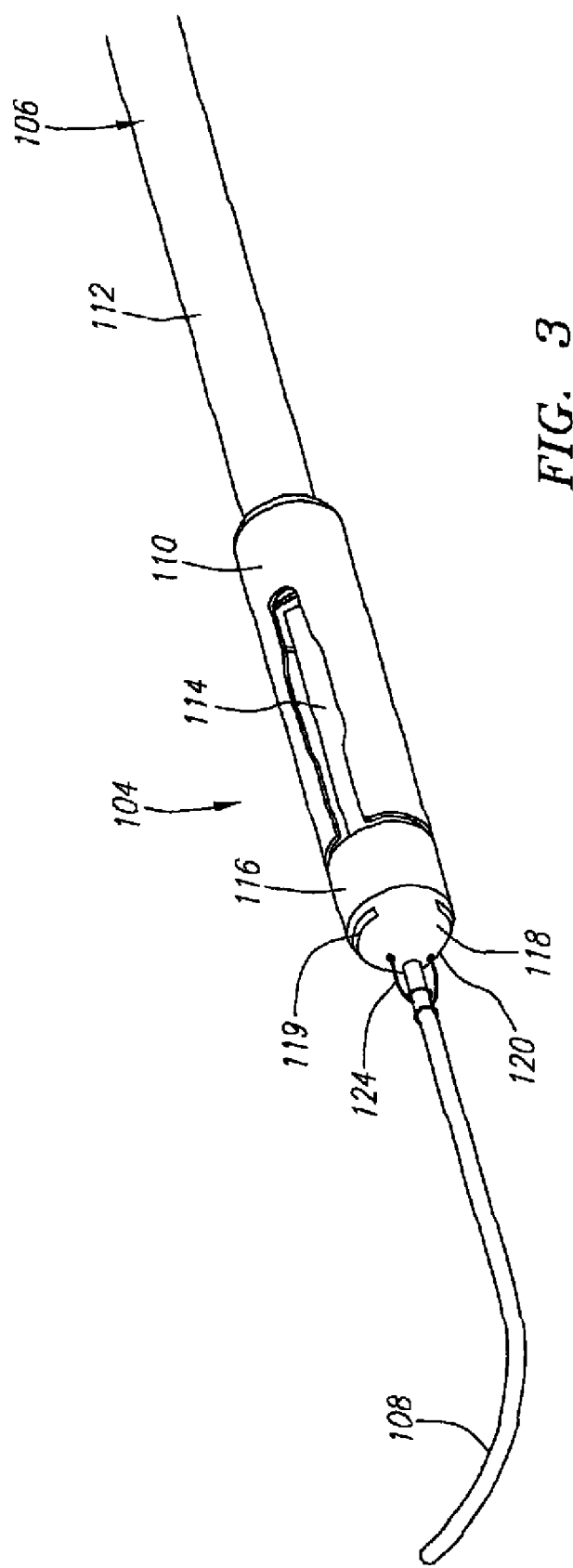
FIG. 3 is a perspective view of a deployment mechanism of the delivery catheter of FIG. 2.
Figure 3A:
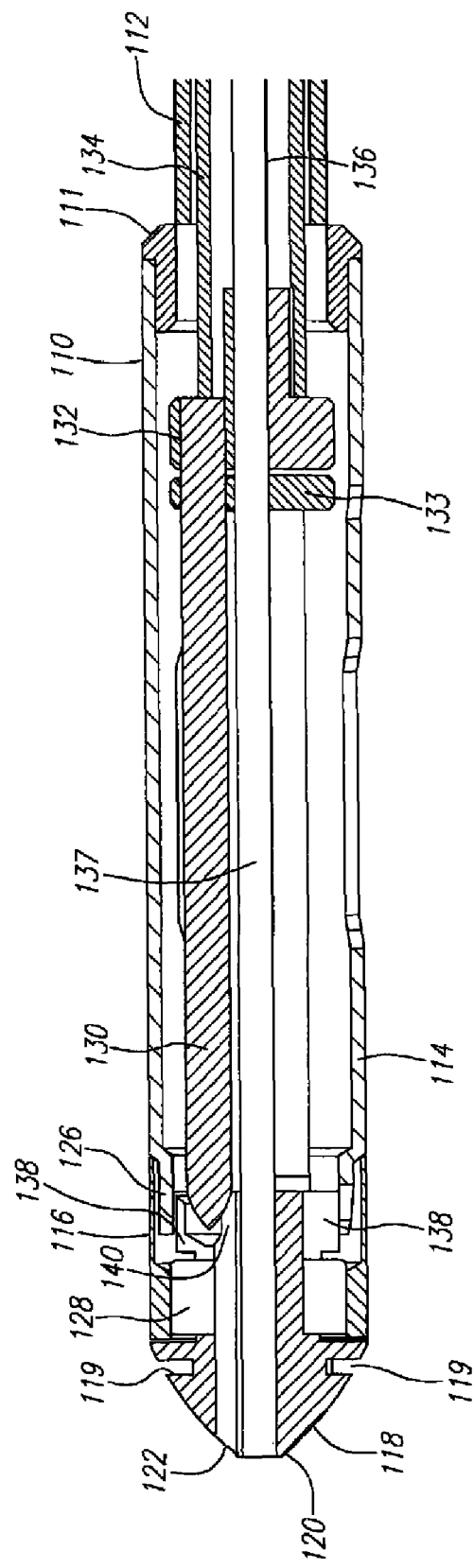
FIG. 3A is a cross-sectional view of the deployment mechanism shown in FIG. 3.
Figure 3B:
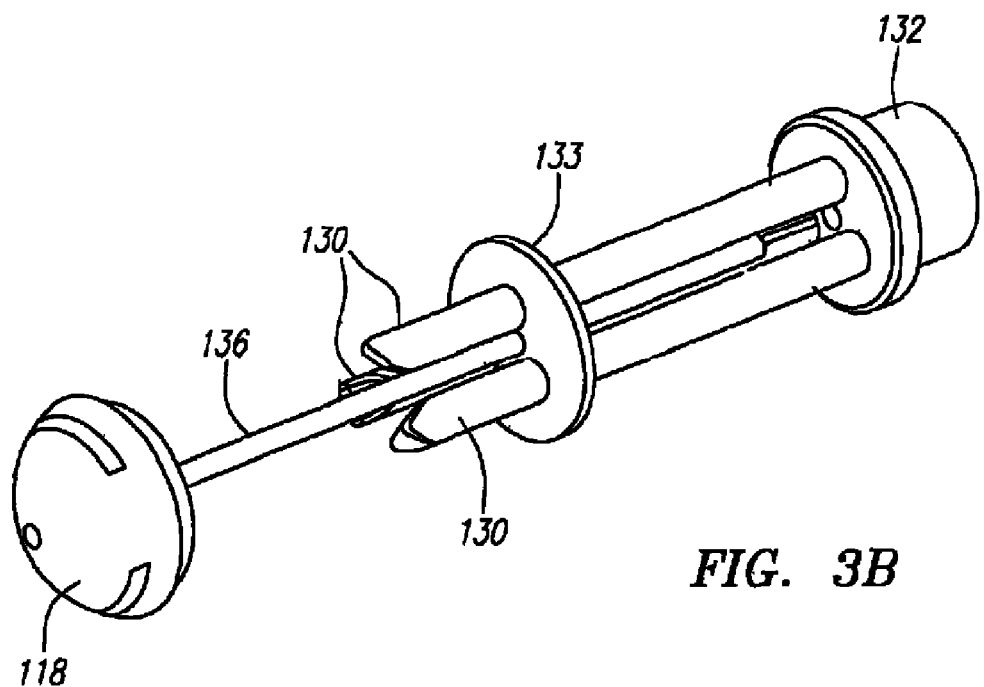
FIG. 3B is a perspective view of several of the internal components included in the deployment mechanism shown in FIG. 3.
Figure 3C:
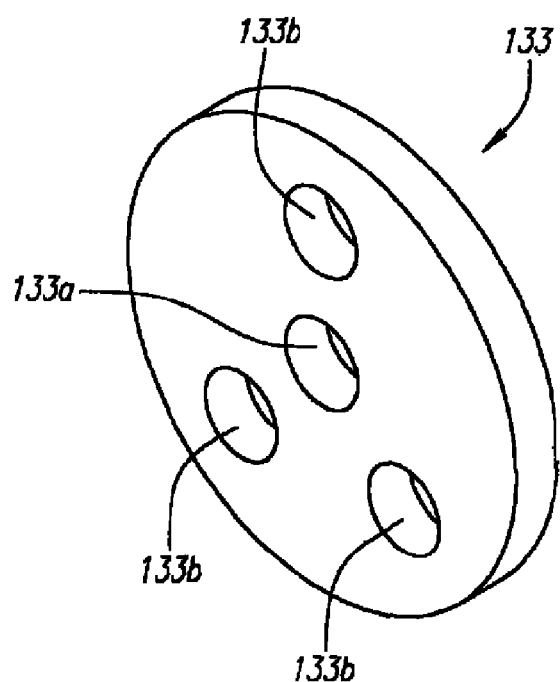
FIG. 3C is a perspective view of a wrapping pin stabilizer.

Turning to FIGS. 3 and 3A, the deployment mechanism 104 is shown in its fully contracted state for use when the mechanism 104 has not yet reached the target site within the body of a patient, such as prior to use and during the delivery process. The deployment mechanism 104 includes a slotted tube 110 that is connected to an outer sheath 112 of the catheter shaft 106, such as by way of the attachment collar 111 (shown in FIG. 3A). Thus, longitudinal movement or rotation of the outer sheath 112 causes longitudinal movement or rotation of the slotted tube 110. The slotted tube 110 is a generally cylindrical body that includes a plurality of longitudinal slots 114 that extend from the distal end of the slotted tube 110 to near its proximal end. In the preferred delivery catheter, the slotted tube 110 includes three slots 114 spaced equidistantly about the circumference of the slotted tube 110. The slots 114 have a length and width that are sufficient to accommodate the extension of portions of the prosthetic valve 30 therethrough, as described more fully below in reference to FIG. 7, described elsewhere herein. The slotted tube 110 is preferably formed of stainless steel or other generally rigid material suitable for use in medical devices or similar applications.

The deployment mechanism 104 may also include a retainer ring 116 and a nosecone 118. Although the retainer ring 116 and nosecone 118 are not necessary parts of the delivery catheter, each of these components may provide additional features and functionality when present. The nosecone 118 is located at the distal end of the delivery catheter and is preferably provided with a generally blunt, atraumatic tip 120 to facilitate passage of the catheter through the patient's vasculature while minimizing damage to the vessel walls. The nosecone 118 is preferably formed of any suitable biocompatible material. In several preferred embodiments, the nosecone is formed of a relatively soft elastomeric material, such as a polyurethane, a polyester, or other polymeric or silicone-based material. In other embodiments, the nosecone is formed of a more rigid material, such as a plastic, a metal, or a metal alloy material. The nosecone may be coated with a coating material or coating layer to provide advantageous properties, such as reduced friction or increased protection against damage. It is also advantageous to provide the nosecone with an atraumatic shape, at least at its distal end, or to form the nosecone 118 of materials that will provide the atraumatic properties while still providing structural integrity to the distal end of the device. The nosecone 118 preferably includes a plurality of throughholes 122 that extend through the length of the nosecone to allow passage of a plurality of tethers 124, which are described more fully below. A pair of slots 119 are formed on the exterior of the nosecone 118. The slots 119 provide a pair of surfaces for a wrench or other tool to grasp the nosecone 118 to enable manual manipulation of the nosecone 118, for purposes to be described below.

The retainer ring 116 is a generally cylindrically shaped ring that is located generally between the slotted tube 110 and the nosecone 118. More precisely, when the deployment mechanism 104 is in the fully contracted state shown in FIGS. 3 and 3A, the retainer ring 116 preferably overlaps a ledge 126 formed on the distal end of the slotted tube 110. Alternatively, the inner diameter of the retainer ring 116 may be formed slightly larger than the outer diameter of the slotted tube 110, thereby allowing the distal ends of the slotted tube 110 to slide within the retainer ring 116 without the need for a ledge 126. In this way, the retainer ring 116 prevents the distal ends of the slotted tube 110 from bowing outward due to pressure caused by the prosthetic valve being stored within the deployment mechanism 104.

The proximal end of the retainer ring 116 engages a bearing 128 that is formed integrally with the nosecone 118, and that allows the nosecone 118 to rotate inside and independently from the retainer ring 116. As described below, the slotted tube 110 is rotated relative to the nosecone shaft 136 and the wrapping pins 130 during some operations of the deployment mechanism, primarily during the expansion and contraction of the prosthetic valve. Without the bearing 128 (or a suitable alternative), the prosthetic valve would tend to bind up within the deployment mechanism and prevent relative rotation between the slotted tube 110 and the wrapping pins 130. Thus, the provision of the bearing 128 engaged with the retainer ring 116 facilitates this rotation of the slotted tube 110, which engages the retainer ring 116.

Additional features of the interior of the deployment mechanism are illustrated in the cross-sectional view shown in FIGS. 3A-G. A plurality of fixed wrapping pins 130 are attached to a wrapping pin hub 132 and extend longitudinally from the hub 132 toward the distal end of the catheter. The preferred embodiment of the delivery catheter includes three wrapping pins 130, although more or fewer are possible. The hub 132 is attached to a wrapping pin shaft 134 that extends proximally from the hub 132 beneath the outer sheath 112 of the catheter shaft 106. Thus, movement or rotation of the wrapping pin shaft 134 causes longitudinal movement or rotation of the hub 132 and the three wrapping pins 130. A wrapping pin stabilizer 133 is slidably attached to the outer surfaces of each of the wrapping pins 130. The pin stabilizer 133 is a generally disc-shaped member having a center hole 133a and three equally spaced throughholes 133b to accommodate the three wrapping pins 130. As described below, in certain orientations of the deployment mechanism 104, the pin stabilizer 133 provides support and stability to the wrapping pins 130 extending distally from the wrapping pin hub 132.

Turning to FIGS. 3D-F, in several of the preferred embodiments, the tethers 124 extend through or are otherwise engaged with the wrapping pins 130. The Figures illustrate several methods by which this is done. In the closed configuration, shown in FIG. 3D, the wrapping pin 130 includes a central lumen 131a through which the tether 124 extends. The lumen 131a extends through the length of the wrapping pin 130 and through the hub 132, allowing the tether to extend proximally to the handle mechanism 102. In the open configuration, shown in FIG. 3E, the wrapping pin 130 includes a channel 131b formed on its underside. The tether 124 is able to be received in the channel 131b, although it is not necessarily retained therein. In the guided configuration, shown in FIG. 3F, the wrapping pin 130 includes a channel 131b formed on its underside. A tether guide 135 is located in the channel 131b, and is preferably attached to the handle housing 152 by welding, adhesive, or other suitable method. The tether 124 is routed through the guide 135, and is thereby retained within the guide 135.

A nosecone shaft 136 is located internally of the wrapping pin shaft 134. The nosecone 118 is attached to the nosecone shaft 136, and the nosecone shaft 136 is slidably received through the wrapping pin hub 132. However, the nosecone shaft 136 is fixed to the wrapping pin stabilizer 133. Thus, longitudinal movement of the nosecone shaft 136 causes longitudinal movement of the nosecone 118 and the pin stabilizer 133, independent of any of the other components of the deployment mechanism 104. However, rotation of the handle housing 152 causes rotation of the nosecone 118, the pin stabilizer 133, and the wrapping pins 130. The nosecone shaft 136 is hollow, thereby defining a guidewire lumen 137 through its center.

A plurality of wrapping pin sockets 138 are formed on the proximal side of the nosecone 118. Each socket 138 is generally cylindrical and has a size adapted to receive the distal portion of a wrapping pin 130 therein. When the distal ends of the wrapping pins 130 are engaged with their respective sockets 138, the sockets 138 provide support and rigidity to the wrapping pins 130. This support and rigidity is particularly needed during the wrapping and unwrapping of the prosthetic valve, as described more fully below. During those operations, a large amount of strain is imparted to each of the wrapping pins 130, which strain is absorbed in part by the sockets 138 formed in the nosecone 118. Each socket 138 is also provided with a hole 140 that provides access to a respective throughhole 122 in the nosecone 118. As described more fully below, this provides a passage for a tether 124 that is contained within each wrapping pin 130 to extend through the hole 140 in each socket, through the throughhole 122 to the distal end of the nosecone 118.

Figure 1:
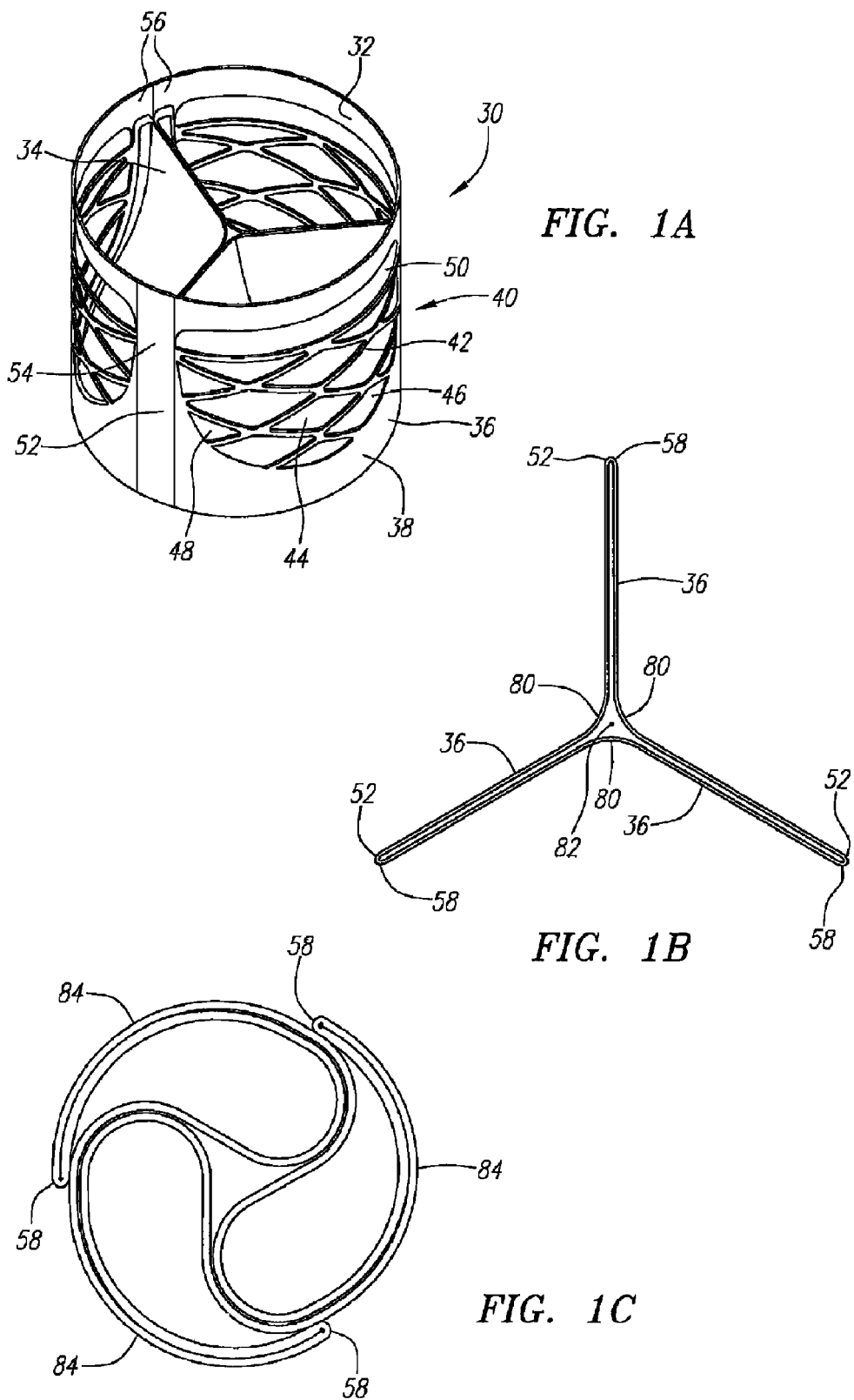
FIG. 1A is a perspective view of a prosthetic valve suitable for use by the delivery catheter of the present invention.
FIG. 1B is a top view of a partially contracted support member illustrating inverted panels to form a "tri-star" shape.
FIG. 1C is a top view of a fully contracted support member illustrating inverted and curled panels to form a "tri-lobe" shape.

Although it is not shown in the cross-sectional view in FIG. 3A, a prosthetic valve 30 such as the type described herein in relation to FIGS. 1A-C—and in the '126 application—may be retained on the wrapping pins 130 in the interior of the slotted tube 110. A suitable method for loading the valve 30 into the device will be described below. The valve 30 is retained in a contracted, multi-lobe state (see, e.g., FIG. 1C) in which each "lobe" is generally wrapped around a respective wrapping pin 130, and held in place there by engagement with the interior surface of the slotted tube 110.

Figure 4:
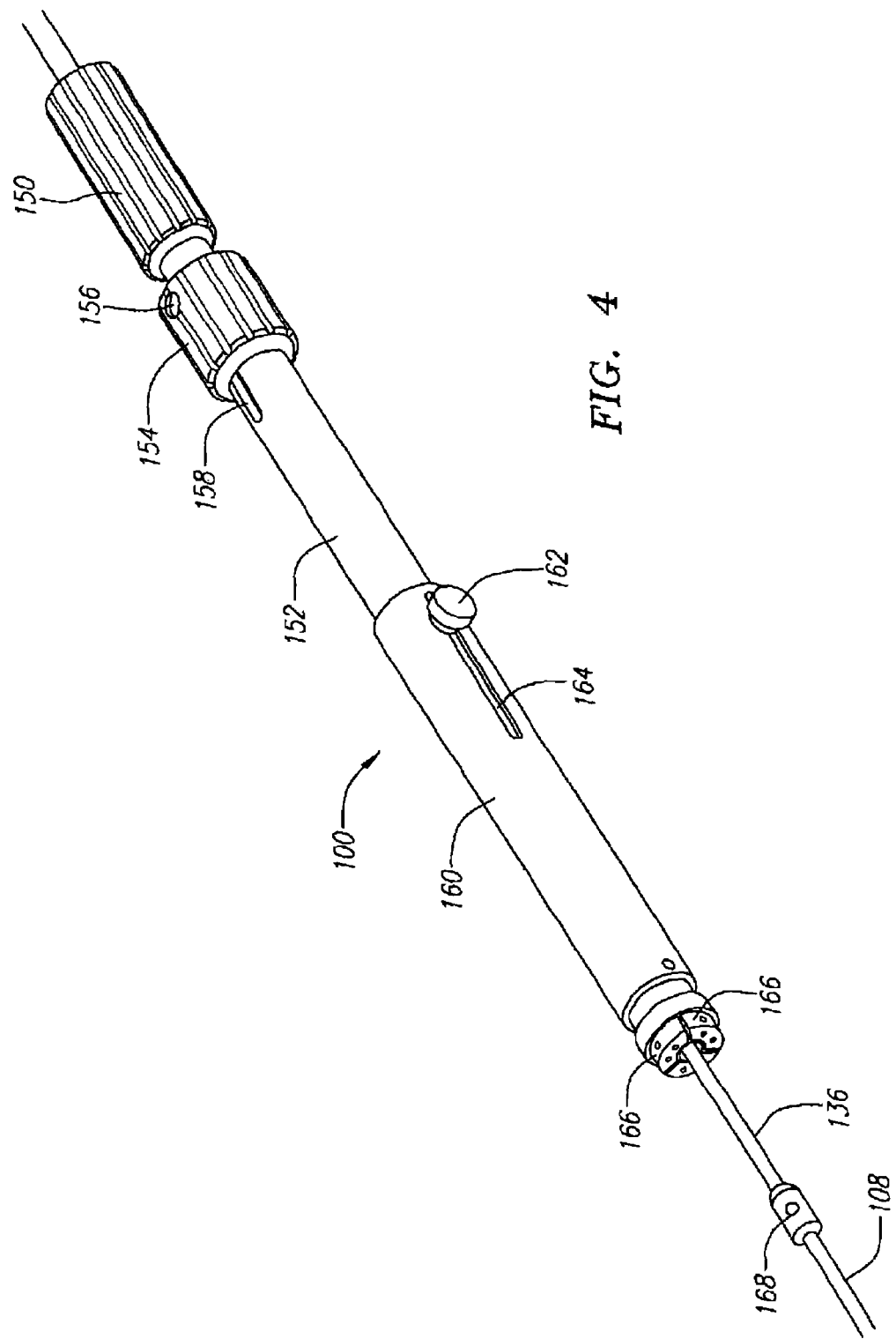
FIG. 4 is a perspective view of a handle mechanism of the delivery catheter shown in FIG. 2.
Figure 5:
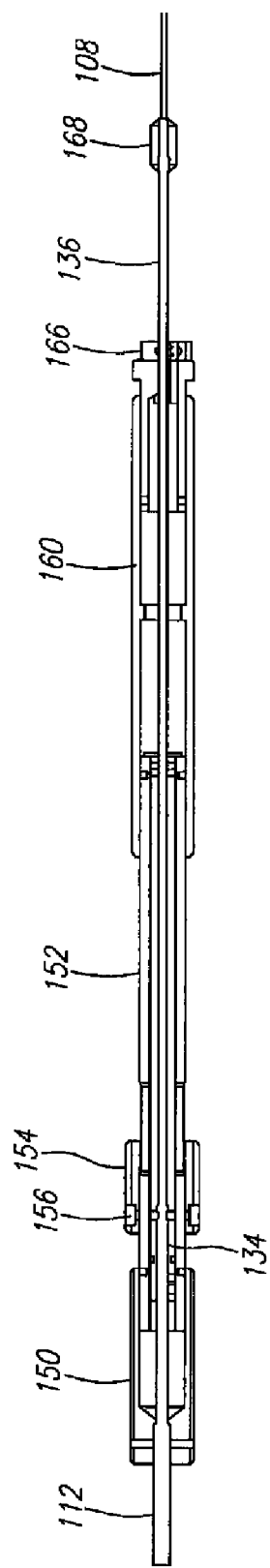
FIG. 5 is a cross-sectional view of the handle mechanism shown in FIG. 4.
Figure 6:
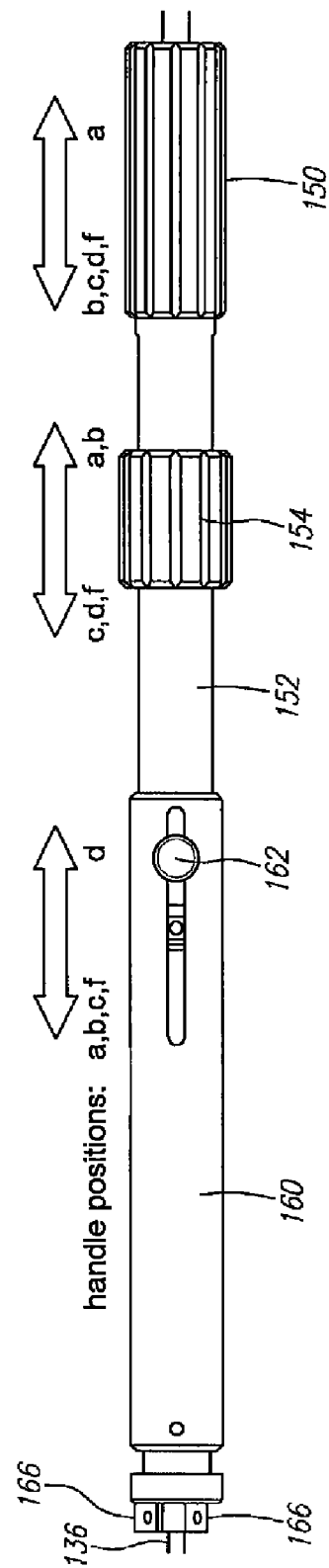
FIG. 6 is a side view of the handle mechanism of the delivery catheter shown in FIG. 2, illustrating several positions corresponding with steps performed during use of the delivery catheter to deliver a prosthetic device.

Turning now to FIGS. 4-6, the handle mechanism 102 will be described. The handle mechanism 102 includes a slotted tube grip 150 that is fixedly connected to the outer sheath 112 while being slidably and rotatably mounted on a handle housing 152. The handle housing 152 is a generally cylindrical hollow shaft. The slotted tube grip 150 is preferably formed of or covered with a corrugated polymer or rubber material to provide the ability to easily grasp and manipulate the grip 150. Similarly, a wrapping pin grip 154, also preferably formed of or covered with a corrugated polymer or rubber material, is slidably mounted to the handle housing 152. The wrapping pin grip 154 includes a bolt 156 that extends through a slot 158 formed in the handle housing 152, to engage the proximal end of the wrapping pin shaft 134. A tether grip 160 is slidably mounted over the proximal end of the handle housing 152. The tether grip 160 is also generally cylindrical, having a slightly larger diameter than the handle housing 152, thereby allowing the tether grip 160 to slide over the handle housing 152 in a telescoping manner. A locking screw 162 extends through a slot 164 formed in the tether grip 160 and into the side of the handle housing 152 near its proximal end. The locking screw 162 allows the user to fix the position of the tether grip 160 relative to the handle housing 152 by screwing the locking screw 162 down.

Three tether clamps 166 extend from the proximal end of the tether grip 160. Each tether clamp 166 is independently clamped to a tether 124 that extends through the catheter to its distal end, as explained in more detail herein. Each tether clamp 166 also includes a spring mechanism (not shown) that provides independent tensioning for each tether 124. The proximal end of the nosecone shaft 136 extends out of the proximal end of the tether grip 160, between the three tether clamps 166, terminating in a small cylindrical nosecone shaft grip 168. The guidewire 108 is shown extending out of the proximal end of the nosecone shaft 136.

The preferred embodiment of the valve delivery catheter so described is intended to be used to deliver and deploy a prosthetic device, such as a prosthetic heart valve, to a patient using minimally invasive surgical techniques. Turning to FIGS. 6-11, a representative method of use of the device will be described. The device is intended to be introduced to the vasculature of a patient over a standard guidewire that has been previously introduced by any known technique, with access via the femoral artery being the preferred method. The guidewire is advanced to the treatment location under x-ray or other guidance, such as to the root of a heart valve, such as the aortic valve. Once the guidewire is in place, the valve delivery catheter 100 is advanced over the guidewire until the deployment mechanism 104 reaches the treatment location. During the delivery process, the deployment mechanism is in the fully contracted state shown, for example, in FIGS. 2 and 3.

Once the deployment mechanism 104 is located near the treatment location, the valve deployment process begins. The guidewire 108 is initially left in place through the deployment process, and is not withdrawn until a particular point in the process defined below. The valve deployment process includes manipulation of the slotted tube grip 150, wrapping pin grip 154, and tether grip 160 located on the handle mechanism 102, which cause a series of manipulations of the slotted tube 110, wrapping pin hub 132 and wrapping pins 130, and the tethers 124, in order to release and deploy the prosthetic valve in a manner that provides control during deployment and the ability to precisely position, re-position, and (if necessary) retrieve the prosthetic valve at any time during the deployment process. FIG. 6 illustrates several of the positions of the components of the handle mechanism 102 during the preferred deployment process. These positions correspond to several of the delivery steps illustrated in FIGS. 7-11.

As noted elsewhere herein, it is possible to provide valves that are contracted into other sizes and orientations (such as two lobes or four or more lobes), which would also include a delivery catheter having a different number of slots in the slotted tube 110 and a different number of wrapping pins 130. For clarity, the present description will focus entirely upon the valve 30 having three panels 36 and three hinges 52, and a delivery catheter 100 having three slots 114 in the slotted tube 110 and three wrapping pins 130.

Figure 7:
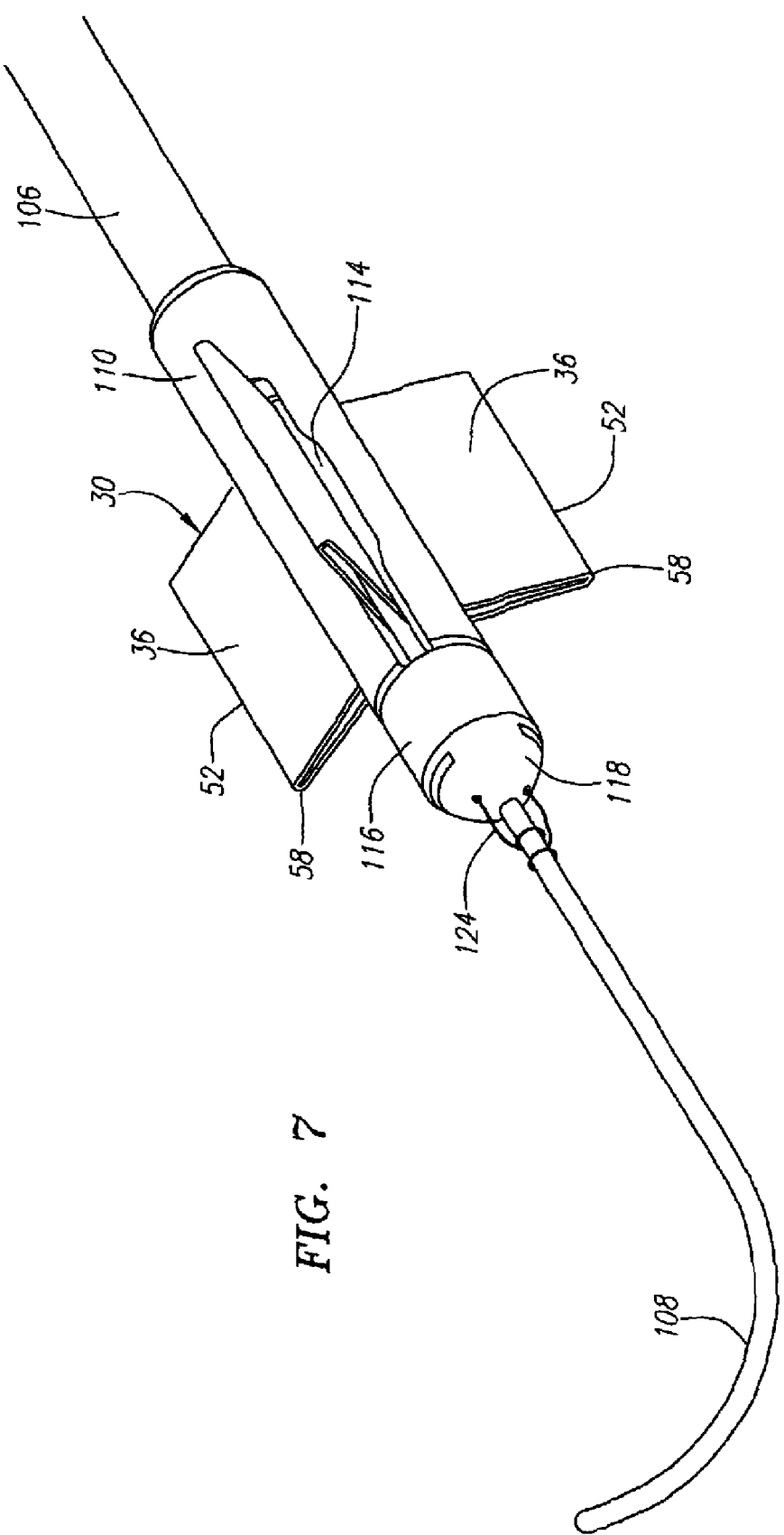
FIG. 7 is a perspective view of the deployment mechanism, shown with a prosthetic valve in a star shape and with the slotted tube fully advanced.

Turning to FIGS. 6 and 7, the first step in deploying the prosthetic valve 30 is to partially expand the contracted valve from the "tri-lobe" shape (see FIG. 1C) to the "tri-star" shape (see FIG. 1B). This is done by causing relative rotation between the slotted tube 110 and the wrapping pins 130. As shown in FIG. 6, this is done by rotating the slotted tube grip 150 around the longitudinal axis of the delivery catheter, thereby causing the slotted tube 110 to rotate around the wrapping pins 130, which are maintained stationary. This relative rotation is facilitated by the provision of the bearing 128 in the nosecone 118 of the deployment mechanism 104, as illustrated in FIG. 3A. As the slotted tube 110 rotates relative to the wrapping pins 130, each of the vertices 58 of the prosthetic valve 30 is caused to extend outward through its respective slot 114 in the slotted tube 110. Rotation of the slotted tube grip 150 is stopped when the valve 30 achieves the "tri-star" shape shown in FIG. 7. At all times during the process up to this point, the adjustable components on the handle mechanism (i.e., the tether grip 160, the wrapping pin grip 154, and the slotted tube grip 150) are maintained in position "a", wherein the tether grip 160 is in its fully retracted position, and the wrapping pin grip 154 and slotted tube grip 150 are each in their fully advanced positions.

Figure 8:
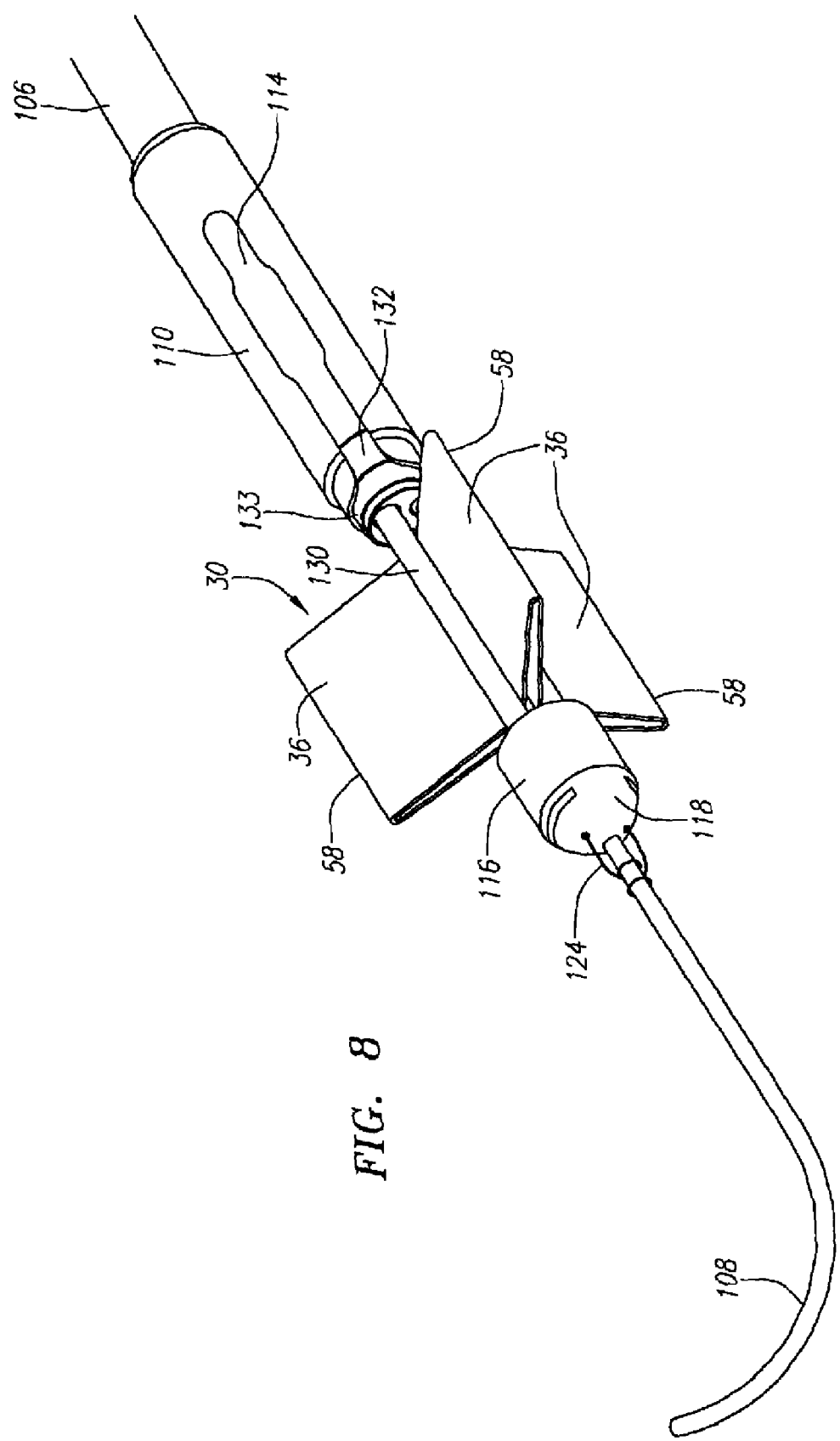
FIG. 8 is a perspective view of the deployment mechanism, shown with a prosthetic valve in a star shape with the wrapping pins fully advanced and with the slotted tube retracted.

Turning next to FIGS. 6 and 8, the next step in the deployment process is to retract the slotted tube 110 to further expose the prosthetic valve 30. This is done by retracting the slotted tube grip 150 to position "b" (FIG. 6) while maintaining the wrapping pin grip 154 and tether grip 160 in the same position "b". Retracting the slotted tube 110 causes the valve 30 to become more exposed, but the valve 30 is maintained in the "tri-star" shape by the wrapping pins 130 which continue to engage each of the three panels 36 of the valve 30. Although not shown in FIG. 8, the distal ends of the wrapping pins 130 also remain seated in the wrapping pin sockets 138 located in the proximal-facing portion of the nosecone 118. In this "b" position, the wrapping pin stabilizer 133 is located just proximally of the valve 30 and is just distal of the wrapping pin hub 132.

Figure 9:
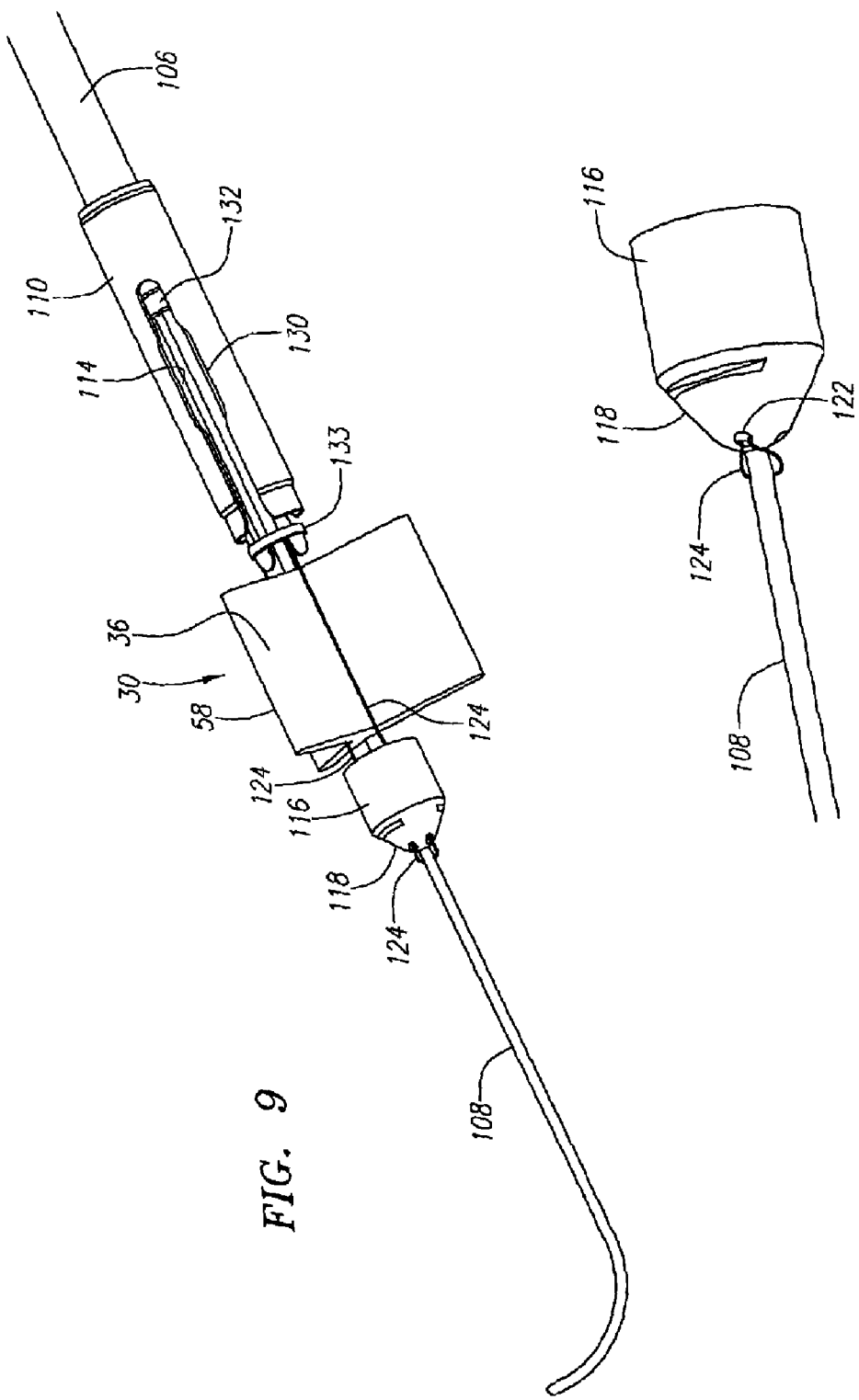
FIG. 9 is a perspective view of the deployment mechanism, shown with a prosthetic valve in a star shape with the wrapping pins and the slotted tube retracted.

Next, turning to FIGS. 6 and 9, the wrapping pins 130 are retracted by retracting the wrapping pin grip 154 to position "c" (as shown in the Figure, transitioning from position "b" to position "c" requires no adjustment of either the slotted tube grip 150 or the tether grip 160). Retracting the wrapping pins 130 causes the wrapping pins 130 to become disengaged from the valve 30 and to retract to the interior of the slotted tube 110. The wrapping pin stabilizer 133, which is fixed to the nosecone shaft 136, slides along the length of the wrapping pins 130 until maximum retraction of the wrapping pins 130, which corresponds to the position shown in FIG. 9, with the stabilizer 133 near the distal ends of each of the wrapping pins 130. In this position, the stabilizer 133 provides support and rigidity to the nosecone shaft 136, which is otherwise only supported by the wrapping pin hub 132. As shown, for example, in FIG. 9, the stabilizer 133 effectively decreases the cantilever length of the nosecone shaft 136, thereby providing it with increased stability. The stabilizer 133 also serves as a backing member for the prosthetic valve 30, preventing the valve 30 from moving proximally as the wrapping pins 130 are retracted. Further, the stabilizer 133 also serves as a guide for the tethers 124 as they extend from the distal ends of the wrapping pins 130.

The valve remains in the "tri-star" position due to the presence of the tethers 124, the spacing of which is maintained by the holes in the stabilizer 133 through which the wrapping pins 130 and tethers 124 extend. In the preferred embodiment shown in FIGS. 9 and 9A, a tether 124 extends through each of the wrapping pins 130, through the hole 140 in the socket 138, through the throughholes 122 in the nosecone 118, and is looped around the guidewire 108 on the distal side of the nosecone 118. The tethers 124 each extend proximally through and within the catheter shaft 106 and is received and retained in its respective tether clamp 166 near the proximal end of the catheter 100. In the position shown in FIG. 9, the tethers 124 are all maintained sufficiently taut that they retain the valve 30 in the "tri-star" orientation shown in the Figure. This corresponds with position "c" of the tether grip 160 relative to the handle housing 152, shown in FIG. 6.

In an alternative embodiment, the tethers 124 may be tensioned by manipulation of the distal connection of the tethers 124 to the guidewire 108. For example, rotation of the nosecone shaft 136 will cause the tethers 124 to wrap around the guidewire 108, thereby providing tension to the tethers 124. Other suitable methods for tensioning the tethers 124 are also contemplated, as will be understood by those skilled in the art.

Figure 10:
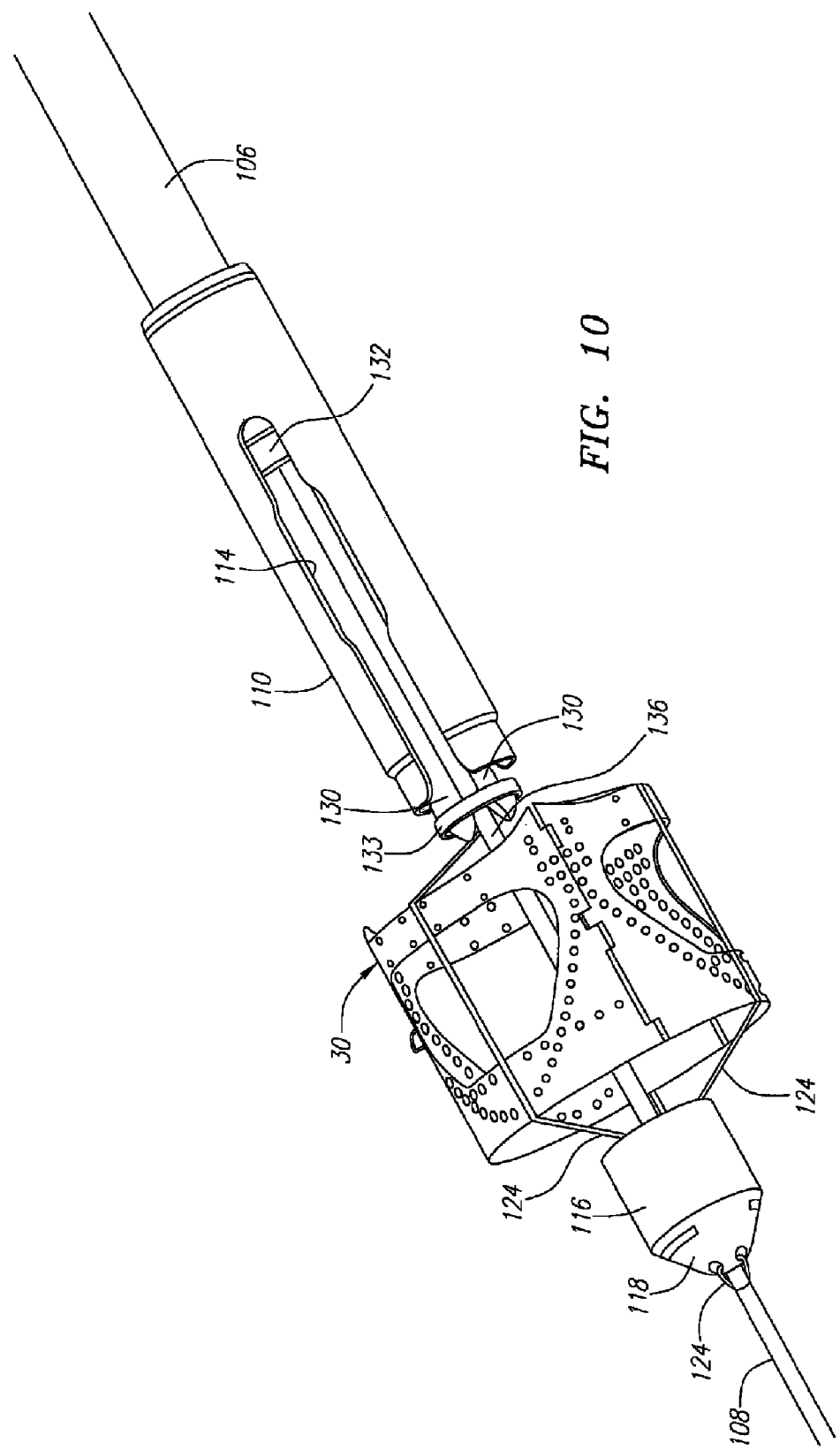
FIG. 10 is a perspective view of the deployment mechanism, shown with a prosthetic valve in expanded shape with tethers retaining the valve in place.

Turning next to FIGS. 6 and 10, expansion of the valve 30 is obtained by loosening the tethers 124 that otherwise hold the valve 30 in the "tri-star" position. This transition is achieved by advancing the tether grip 160 to position "d", as shown in FIG. 6. (Note: Transitioning from position "c" to position "d" requires no adjustment of either the slotted tube grip 150 or the wrapping pin grip 154). Advancement of the tether grip 160 relative to the handle housing 152 creates slack in the tethers 124, which slack is taken up by the radial expansion of the valve 30. In the typical deployment, the valve 30 will automatically fully expand to the deployment position shown in FIG. 10 when the tension is released from the tethers 124. For those situations in which the valve 30 does not automatically expand, or when the valve only partially expands, one or more alternative mechanisms and/or methods may be utilized to obtain full expansion. Several of these preferred mechanisms and methods are described below in Section B.

It is significant that, in the position shown in FIG. 10, the tethers 124 no longer interfere with the expansion of the valve 30, but they remain in control of the valve 30. In this position, it is possible to make any final positional adjustments of the valve 30, if necessary. This can be done by simply advancing or withdrawing the catheter 100, which tends to drag or push the valve 30 along with it. This may also be facilitated by slight advancement of the wrapping pin grip 154 and/or retraction of the tether grip 160, each of which actions will tend to apply tension to the tethers 154. In this manner, the valve position may be adjusted by the user while the valve is in its fully expanded state, under control of the tethers 124.

Alternatively, the valve 30 may be partially or fully contracted once again by increasing the tension on the tethers 124, as by retracting the tether grip 160 relative to the handle housing 152. (I.e., moving from position "d" to position "c" in FIG. 6). If necessary, the valve 30 may be fully contracted by retracting the tether grip 160, and then the deployment mechanism 104 may be fully restored to the undeployed position by simply reversing the above steps, in order. (I.e., moving to position "c", then position "b", then position "a"). This reversal of the process includes a step of advancing the wrapping pins 130 back over the contracted valve panels as the valve 30 is maintained in the "tri-star" shape. This process is facilitated by the presence of the tethers 124, which act as guides for the wrapping pins 130 to "ride up" over the edges of the valve panels under the guidance of the tethers 124. Once the wrapping pins 130 are in place, the slotted tube 110 is advanced over the valve 30, with each of the vertices of the valve "tri-star" extending through its respective slot 114. The slotted tube 110 is then rotated relative to the wrapping pins 130 and valve 30, causing the valve to transition to the fully contracted "tri-lobe" shape fully contained within the slotted tube 110. At that point, the delivery catheter may be removed from the patient without deploying the valve 30. Any or all of these adjustment or removal steps may be taken, depending upon the clinical need or depending upon any situation that may arise during the deployment procedure.

Figure 11:
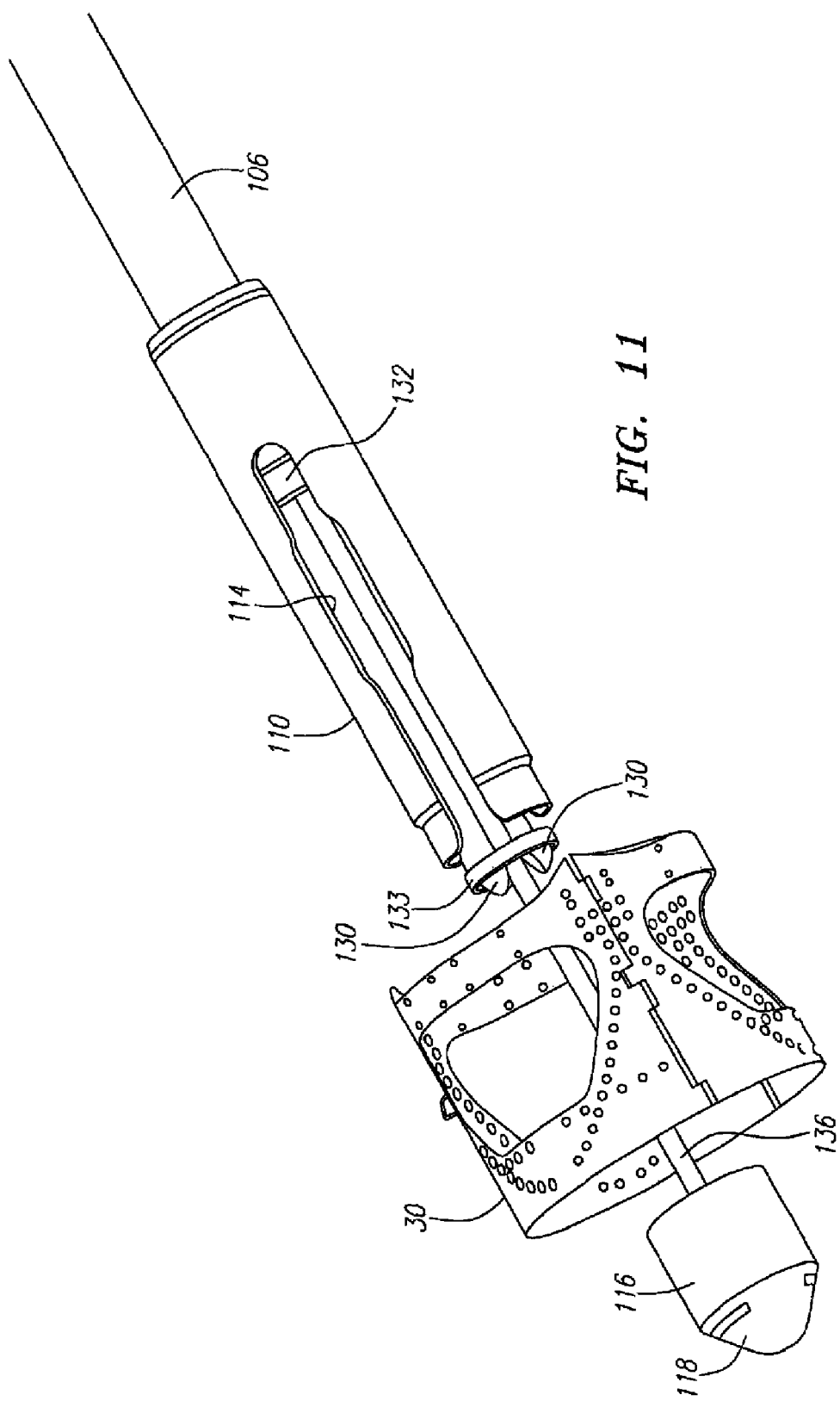
FIG. 11 is a perspective view of the deployment mechanism, shown with a prosthetic valve in expanded shape, and showing the guidewire and tethers withdrawn to release the valve.

Turning to FIGS. 6 and 11, assuming that the valve 30 is placed in its final position and is ready to be released, the valve is released from the delivery catheter 100 by retracting the guidewire 108 to a position such that the distal end of the guidewire 108 no longer extends past the distal end of the nosecone 118 of the delivery catheter 100. At this point, the tethers 124 are released from their engagement with the guidewire 108. Preferably, the tethers 124 are then retracted at least into the wrapping pins 130, and may alternatively be fully retracted through and from the proximal end of the delivery catheter 100. This is reflected as handle position "f" in FIG. 6, in which the tether grip 160 is retracted at least to its initial position, and no change is made to the positions of either the wrapping pin grip 154 or the slotted tube grip 150. As shown in FIG. 11, the valve 30 is completely free from the delivery catheter 100. The nosecone 118 remains distal of the valve 30, and the nosecone shaft 136 extends through the body of the valve 30.

To complete the delivery process, the delivery catheter is preferably contracted to its pre-delivery state by advancing the wrapping pins 130 into engagement with the nosecone 118 by advancing the wrapping pin grip 154 on the handle back to position "a", then by advancing the slotted tube 110 into engagement with the retainer ring 116 by advancing the slotted tube grip 150 on the handle back to position "a". At this point, the delivery catheter 100 may be removed from the patient, leaving the prosthetic valve 30 in place.

B. Variations in Construction, Components, and/or Features of Delivery Device

Preferred delivery catheters and methods of use are described above. A number of variations of several of the components, features, and other aspects of the device have been contemplated, and are described below.

Figure 12A:
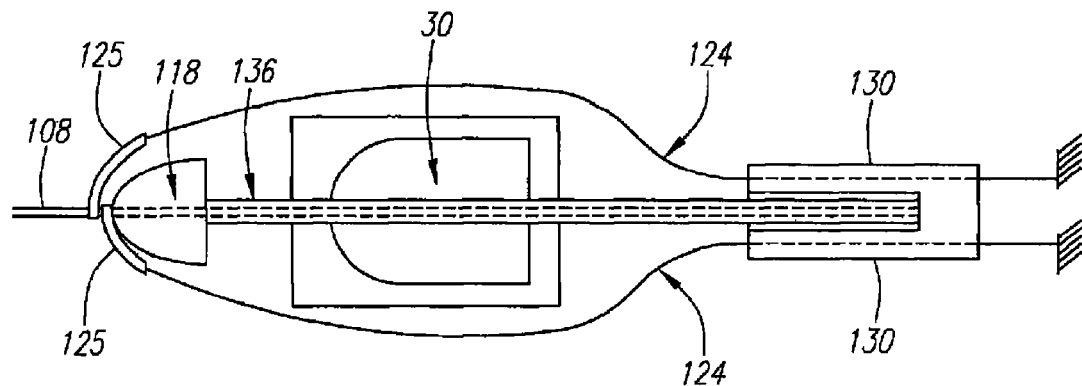
FIGS. 12A-B are side cross-sectional and end views, respectively, of a portion of the distal end of a delivery catheter, illustrating an eyelet formed on the ends of each tether.
Figure 12B:
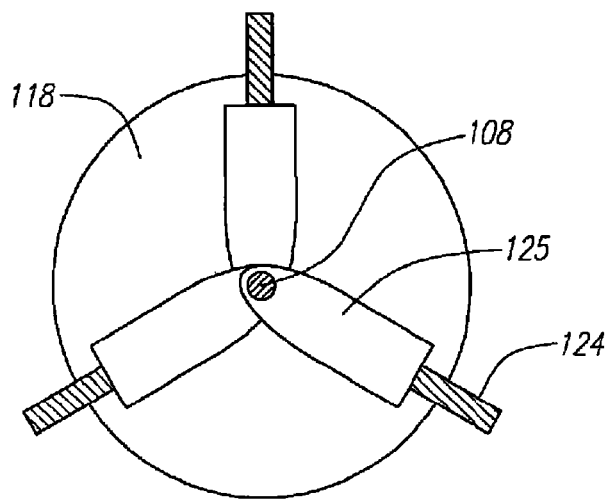

Turning first to FIGS. 12A-B, an alternative method of connecting the tethers 124 to the guidewire 108 is shown. In the embodiment described above, the tethers 124 are looped over the guidewire 108. In the embodiment shown in FIGS. 12A-B, each tether 124 has an eyelet 125 formed at its distal end. The eyelet 125 is connected to the tether by an adhesive bond, or by crimping, or by any other suitable method. Each eyelet 125 has a hole formed at its distal end that is large enough to accommodate the guidewire 108 extending therethrough. The eyelet 125 may have a generally curved shape to rest alongside the nosecone 118, and a terminal end that is generally perpendicular to the longitudinal axis defined by the guidewire 108.

Figure 12C:
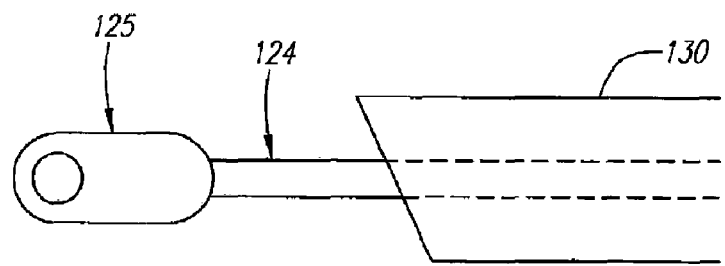
FIGS. 12C-D are side cross-sectional views of a first wrapping pin having no recess, and a second wrapping pin having an eyelet recess formed therein.
Figure 12D:
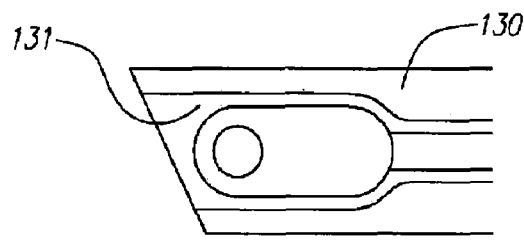

Turning to FIGS. 12C-D, an optional recess 131 may be formed in the distal end of each of the wrapping pins 130. The recess 131 is preferably formed having a shape and size to accommodate the eyelet 125 that is optionally provided at the distal end of each of the tethers 124. Accordingly, when no recess 131 is available (see, e.g., FIG. 12C), the eyelet 125 may be unable to be withdrawn into the lumen provided for passage of the tether 124. When a recess 131 is provided (see, e.g., FIG. 12D), the eyelet 125 is retracted into the recess 131 and does not extend out of the distal end of the wrapping pin 130.

Figure 12E:
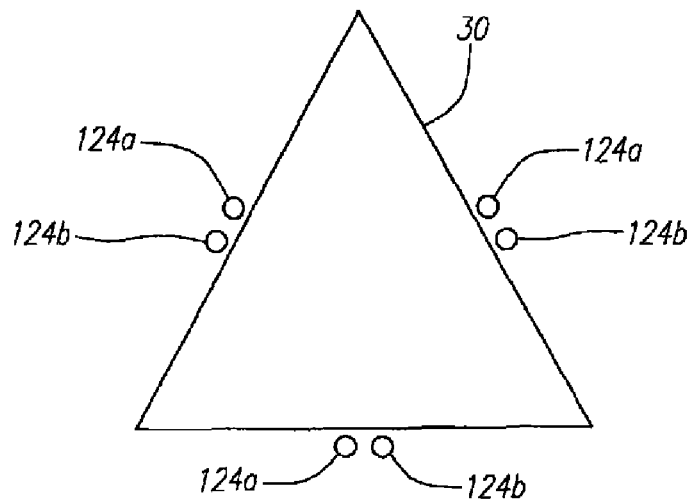
FIG. 12E is an end cross-sectional view of a prosthetic valve partially restrained by three dual tethers.
Figure 12F:
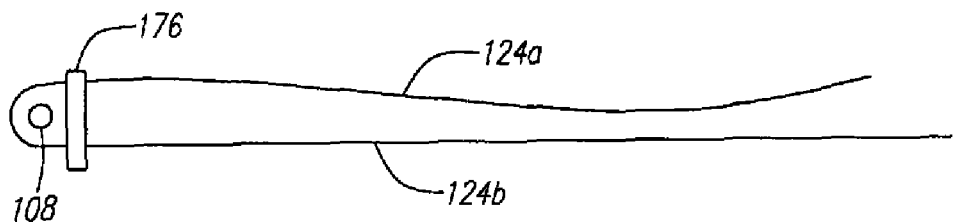
FIGS. 12F-G are illustrations of two methods for selectively attaching dual tethers to a guidewire.
Figure 12G:
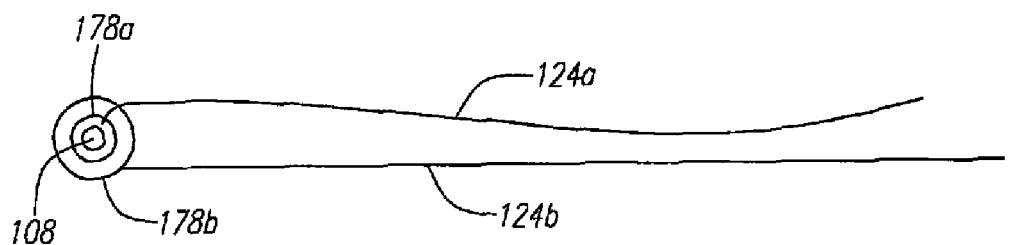

FIG. 12E illustrates an embodiment including a plurality of dual or redundant tethers 124a-b. As shown in the Figure, a pair of tethers 124a-b are provided on each of the panels of the valve 30. The dual tethers 124a-b may be provided to increase tether strength, where needed, or to provide redundancy in the case of failure of one of the tethers. FIGS. 12F and 12G illustrate two possible methods for attaching the dual tethers 124a-b to a guidewire 108. In the first method, shown in FIG. 12F, a collar 176 is formed near the distal ends of and is attached to both of the tethers 124a-b near their distal ends, thereby forming a loop through which the guidewire 108 extends. In this construction, the loop will remain even if one of the tethers fails. In the second method, shown in FIG. 12G, each of the tethers 124a-b includes a separate attachment loop 178a-b, through which the guidewire 108 extends. In each method, the tethers 124a-b are released when they are disengaged from the guidewire 108 in the manner described above.

Figure 13:
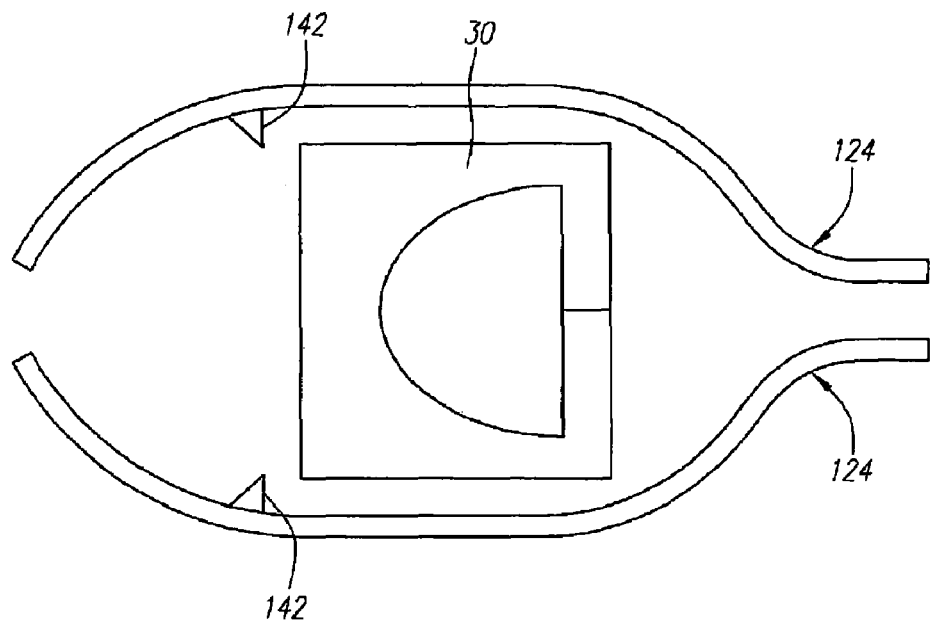
FIG. 13 is a side view of a portion of a delivery catheter illustrating a valve stop formed on each tether.

Turning to FIG. 13, a valve stop 142 may be provided on each of the tethers 124. Each valve stop 142 is in the form of a small cleat, barb, tab, or other transverse extension from the tether 124. The valve stop 142 is intended to provide another mechanism to prevent the valve 30 from slipping or migrating relative to the tethers 124 when the tethers 124 are in engagement with the valve 30. Thus, the valve stop 142 is located at a particular known position on each tether 124 to provide an optimal amount of control to the device 100 when the tethers 124 are engaged with the valve 30.

Figure 14A:
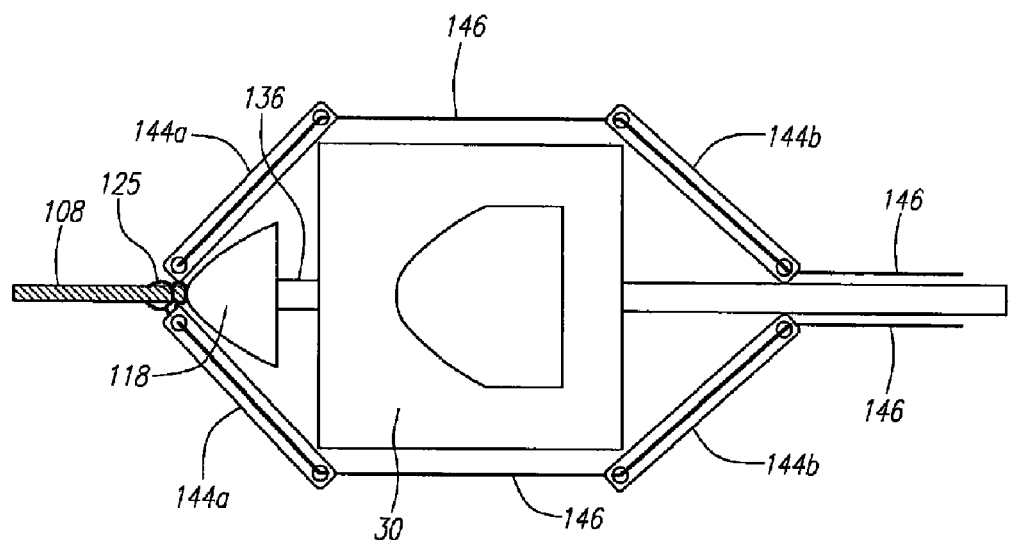
FIGS. 14A-B are side partial cross-sectional views of a portion of a delivery catheter illustrating tethers including linkage members.
Figure 14B:
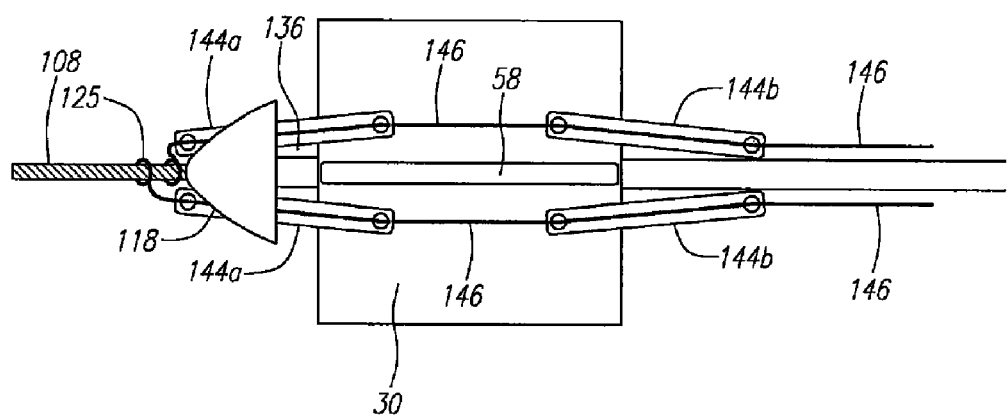

FIGS. 14A-B illustrate tethers formed of linkages 144 and tether sections 146. Each tether includes an eyelet 125 at its distal end connecting the tether to the guidewire 108. The eyelet 125 is connected directly to a first linkage member 144a, which may comprise a relatively rigid member formed of a metallic material, a rigid polymeric material, or the like. The linkage 144 is of a length sufficient to accommodate the valve 30 in its expanded state, as shown in FIG. 14A. The first linkage 144a is connected to a tether section 146 that extends through the length of the valve 30, and then connects to a second linkage member 144b. The second linkage member 144b then connects to another section of the tether 146, which extends proximally into the remainder of the delivery catheter. Each linkage member 144a, 144b includes a pivot at each end thereof, thereby enabling the linkage member 144a, 144b to pivot relative to the member to which it is attached. Thus, when the tethers are relaxed, the valve 30 is allowed to expand, as shown in FIG. 14A. However, when the tethers are pulled taut, the linkages 144a, 144b pivot, thereby causing the tethers to become taut and to convert the valve to its "tri-star" shape, as shown in FIG. 14B. Preferably, the nosecone 118 is provided with slots that accommodate the first linkage members 144a when they are pulled taut in the position shown in FIG. 14B.

Figure 15:
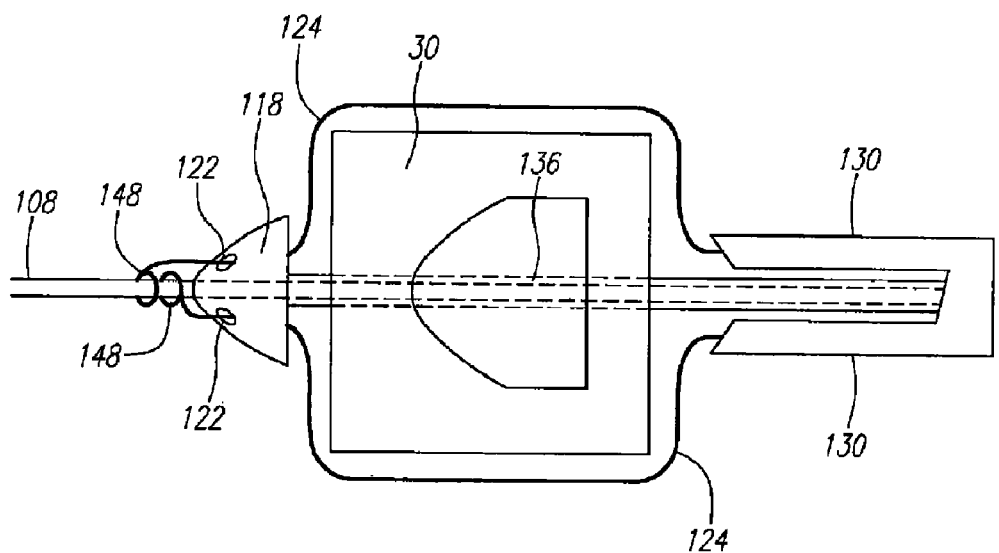
FIG. 15 is a side view in partial cross-section of a delivery catheter illustrating tethers having loops that are routed through throughholes in the nosecone.

FIG. 15 illustrates a slight variation of the preferred embodiment described above. In this embodiment, the tethers 124 each include a loop 148 formed on their distal ends. Each loop 148 is adapted to engage the guidewire 108. The tethers 124, in turn, are routed through throughholes 122 formed in the nosecone 118, as described above. Each tether 124 is then routed through a lumen formed in its respective wrapping pin 130. This particular routing orientation provides a mechanical advantage over other routing orientation because the tethers are captured by the nosecone 118 and wrapping pins 130 in close relation to the valve 30. This orientation also results in less migration of the tethers from side-to-side relative to the valve 30.

Figure 16A:
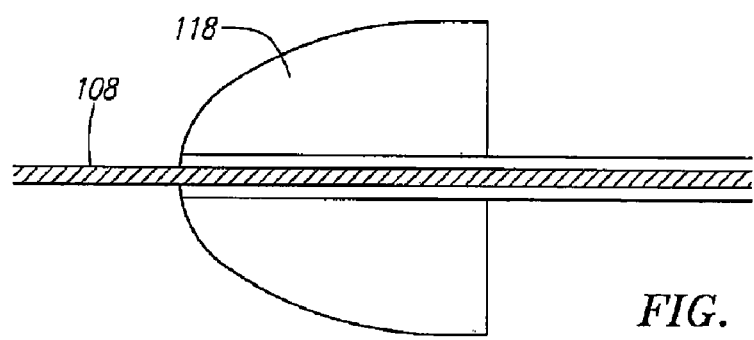
FIGS. 16A-B are a side view in partial cross-section and an end view showing a slotted nosecone.
Figure 16B:
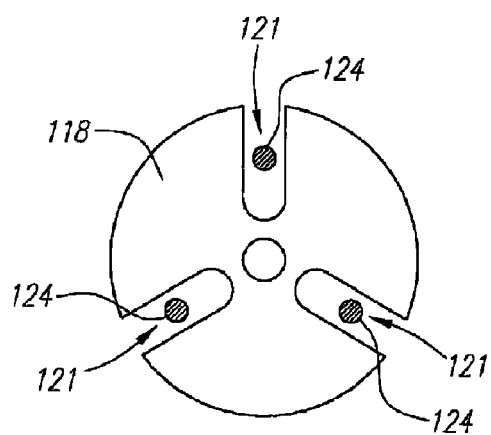

Turning next to FIGS. 16A-B, an alternative method for routing the tethers 124 in and around the nosecone 118 is to provide a plurality of slots 121 on the exterior of the nosecone 118. Each slot 121 is adapted to receive and retain a tether 124 when the tethers 124 are pulled taut. The slots 121 also allow the tethers to arise out of and disengage from its respective slot 121, for example, when the tethers 124 are slack and the valve 30 expands.

Figure 17:
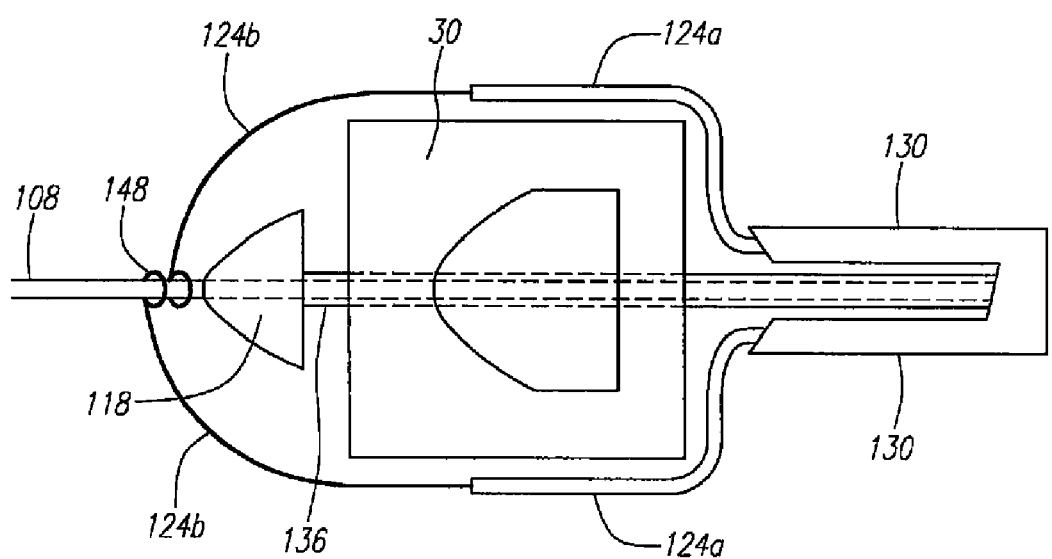
FIG. 17 is a side view in partial cross-section of a delivery catheter illustrating tethers having primary and secondary sections.

FIG. 17 illustrates another embodiment containing tethers formed of two separate components, including a thick, or broad primary tether 124a and a thin, or narrow secondary tether 124b. The primary tether 124a may be formed of a round or flat wire, and may be provided as either a straight component or it may be provided with a degree of shape memory. The secondary tether 124b may be made from a finer, smaller diameter material that is less traumatic to the vessel when it is pulled from between the valve 30 and the vessel. The secondary tether 124b may also be more easily retracted through the wrapping pins 130. Although a two-component tether 124 is shown, it should be appreciated that three or more components may also be incorporated to make up the tether 124 and to obtain various performance characteristics.

Figure 18A:
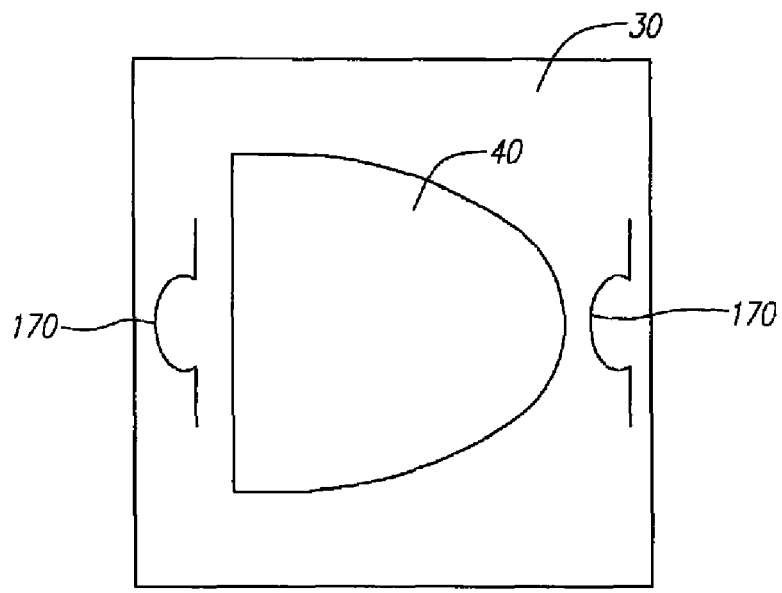
FIGS. 18A-B are side views of a portion of a prosthetic valve having loops for engaging a tether to prevent migration.
Figure 18B:
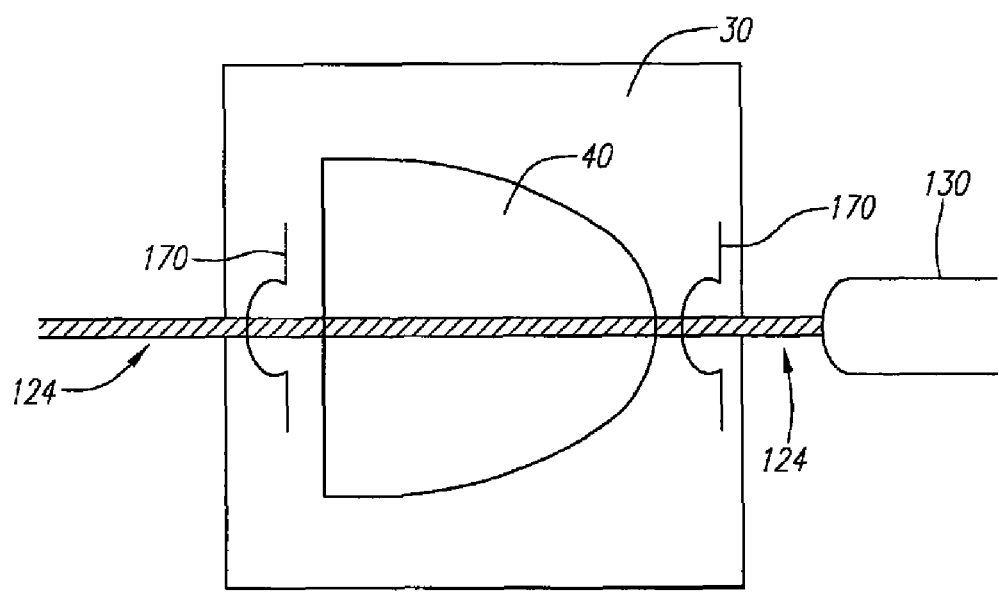

Turning next to FIGS. 18A-B, a pair of loops 170 are shown formed on the external surface of the valve 30. The loops 170 are intended to provide an engagement member on the surface of the valve 30 for the tethers 124 to engage to prevent the tethers 124 from migrating on the surface of the valve 30. For example, if the tether 124 migrates from the centerline of a valve panel 36, it may no longer have the ability to cause the valve panel 36 to invert or to restrain it in its inverted shape. By providing the loops 170, such migration of the tethers 124 is substantially prevented. It will be appreciated that mechanisms other than loops 170 may also be provided to restrain tether migration. For example, holes, barbs, slots, bumps, or other members may be provided on the surface or integrated into the body of the valve panel 36 to substantially restrain tether migration. One or more such members may be sufficient to provide sufficient restraining capability.

Figure 19A:
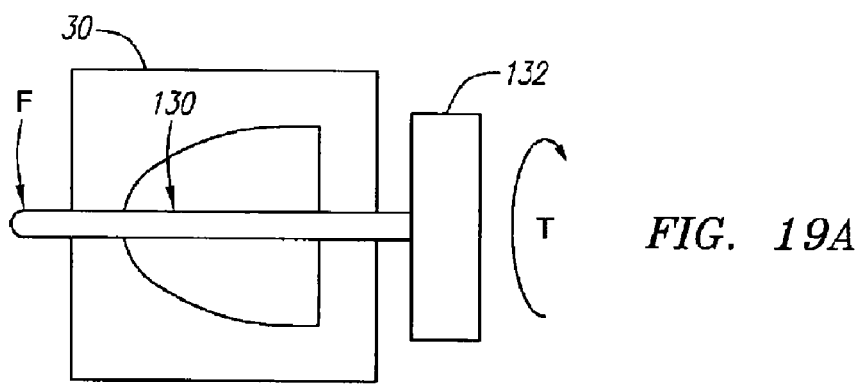
FIGS. 19A-D are side views of several embodiments of wrapping pins.
Figure 19B:
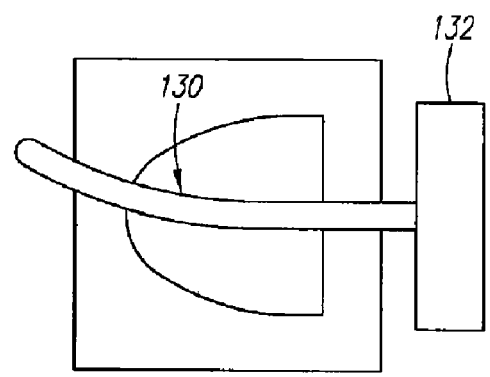
Figure 19C:
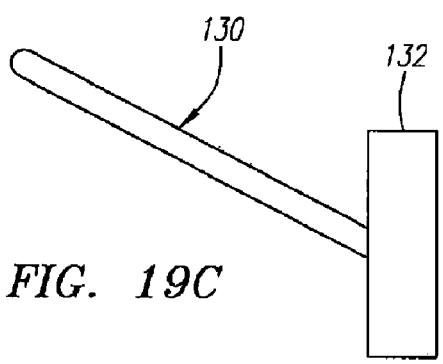
Figure 19D:
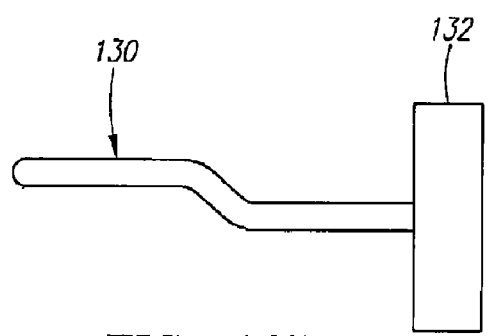

Turning to FIGS. 19A-D, several alternative wrapping pin embodiments are illustrated. The alternative embodiments represent several methods by which wrapping pin deflection may be overcome. As shown, for example, in FIG. 19A, when the wrapping pin hub 132 is rotated to cause wrapping up of a prosthetic valve 30 by the wrapping pins 130, an amount of torque "T" is imparted to the hub 132, and a corresponding deflecting force "F" is imparted to the distal end of the wrapping pin 130. The deflecting force "F" tends to cause the wrapping pin 130 to deflect in the direction of the deflecting force "F", which tends to interfere with the wrapping procedure. To counteract the deflection force, the wrapping pin 130 may be formed having a gradual curving shape, as shown in FIG. 19B, to offset the deflection and to provide more even wrapping of the valve 30. The degree and nature of the curvature will vary depending upon the materials, sizes, and other properties of the delivery device and the valve, although the curvature will typically be directed toward the deflecting force. Alternatively, the wrapping pin 130 may be attached to the hub 132 at a fixed angle, or canted, as illustrated in FIG. 19C. Once again, the cant angle may be determined and will vary. Another alternative is shown in FIG. 19D, in which the wrapping pin 130 is provided with an offset between its proximal and distal ends. Once again, the degree of offset may be varied according to need for a given device.

Turning to FIGS. 20A-B, in several additional alternative embodiments, the wrapping pins 330 are not fixed in shape or orientation relative to the hub 332. In several such embodiments, the wrapping pins 330 include articulating segments 331 connected by rotating joints 332, thereby allowing each wrapping pin 330 to move radially relative to the longitudinal axis of the device. The concerted movement of the multiple wrapping pins 330 (three pins being preferred, but more or fewer also being possible) allows the structure to act as a gripper for manipulating the prosthetic valve 30. In the preferred embodiments, movement of each articulated wrapping pin 330 is independently controlled, thereby allowing the user to move each articulated wrapping pin 330 independently from a position generally comparable to that of the fixed wrapping pins 330 illustrated in the drawings (see FIG. 20A), to a position substantially radially outwardly spaced from the longitudinal axis of the device (see FIG. 20B). Thus, the close-in position (FIG. 20A) is suitable for restraining the valve in its contracted or "tri-star" shape, while the radially spaced position (FIG. 20B) is suitable for releasing the valve to its expanded state, or for retrieving the valve from its expanded state in order to transition the valve back to its contracted state.

Figure 21A:
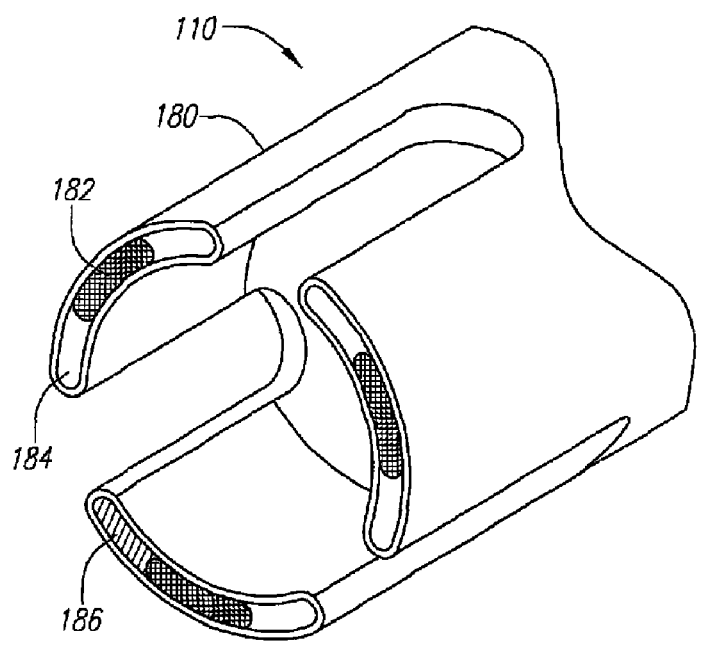
FIGS. 21A-B are an end perspective view in partial cross-section and a top view in partial cross-section of a slotted tube.
Figure 21B:
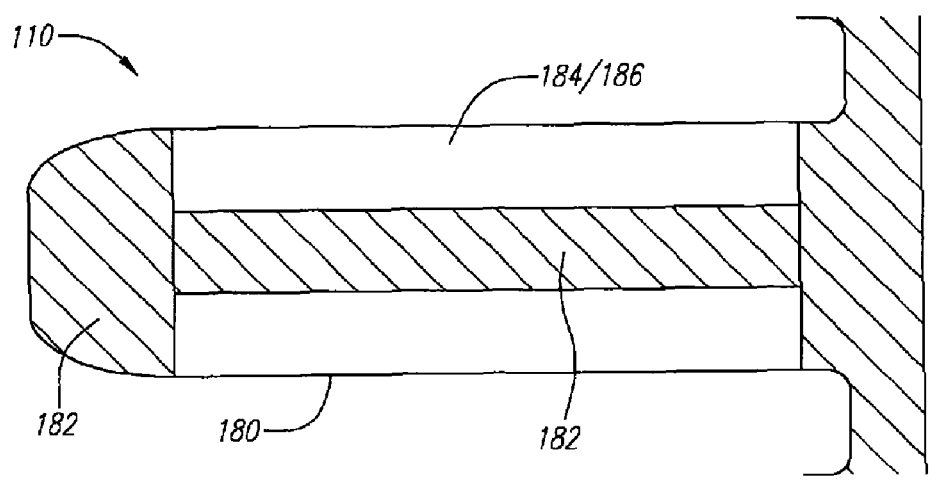

FIGS. 21A-B illustrate an alternative construction for the slotted tube 110. In this construction, each of the longitudinal members 180 forming the slotted tube 110 includes an internal base portion 182 formed of a rigid material such as stainless steel or other metallic material, or a rigid polymeric material. The base portion 182 is intended to provide strength and resiliency to the slotted tube 110 to perform its functions of receiving, retaining, and manipulating the valve 30 in response to manipulations of the components contained on the handle mechanism 102 of the delivery catheter. Surrounding the base portion 182 of the slotted tube 110 are a number of air gaps 184 and/or filled sections 186 that are filled with a more flexible, less rigid material relative to the material forming the base portion 182. A wide variety of filler materials are possible, including several polymeric material such as polyurethane, or other soft materials such as one or more silicone based materials. The purpose for the air gaps 184 and/or filled portions 186 are to provide a less traumatic construction to reduce the likelihood of causing damage to the valve 30 or any of its panels 36 or hinges 52 while the valve is being loaded, stored, or deployed. By providing an air gap 184 or filled sections 186 on the edges of the longitudinal sections 180 of the slotted tube 110, the valve 30 is more protected during roll-up or deployment of the valve, during which time the edges of the longitudinal members 180 impose force against the valve panels 36 to cause them to roll up within the deployment mechanism 104 or to deploy out of the slotted tube 110.

Figure 21C:
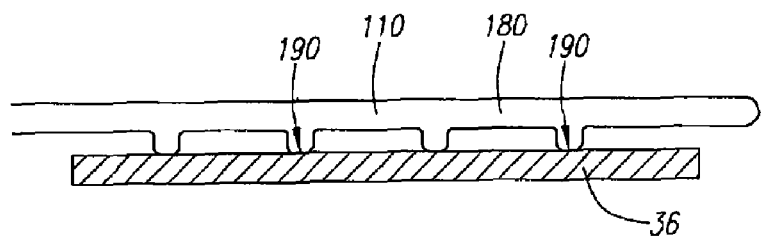
FIG. 21C is a side cross-sectional view of a slotted tube having runners and a valve panel in its contracted state.

Turning to FIG. 21C, another mechanism for protecting the valve panels 36 while they are retained within the slotted tube 110 is comprised of a series of runners 190 formed on the internal-facing surfaces of the longitudinal members 180 making up the slotted tube 110. The runners 190 provide a raised surface upon which the panels 36 will ride to minimize the contact between the panels 36 and the slotted tube 110. The runners 190 also serve to decrease friction between the two components and decrease the amount of abrasion that is imparted to the panels.

Figure 22A:
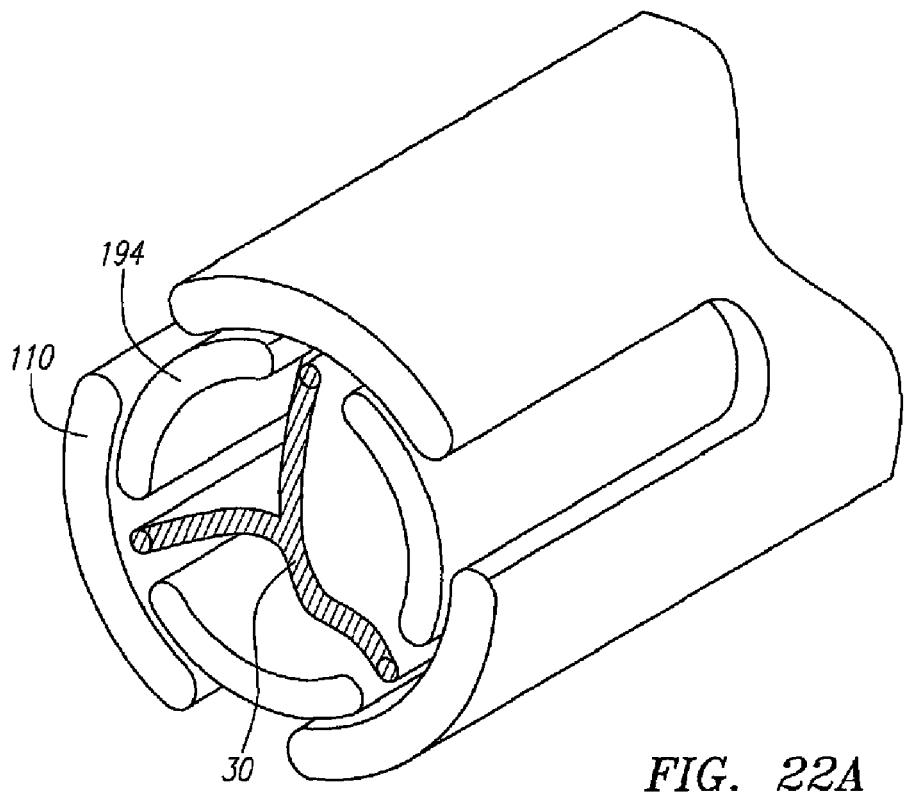
FIGS. 22A-B are a perspective view and an end view, respectively, of an alternative deployment mechanism for a delivery catheter.
Figure 22B:
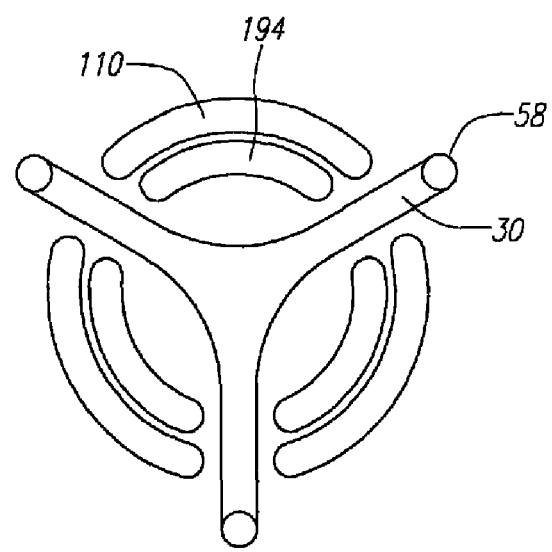

FIGS. 22A-B illustrate another alternative construction for a portion of the deployment mechanism 104 of the delivery catheter 100. In this alternative construction, the wrapping pins 130 are not needed. Instead, an inner slotted tube 194 is provided coaxially with and interior to the outer slotted tube 110. As the inner slotted tube 194 is rotated relative to the outer slotted tube 110, the valve 30 is converted from a "tri-star" shape to a "tri-lobe" shape, as shown, for example, in FIG. 22A. Reversing the relative rotation causes the valve 30 to extend out of the slots formed in each of the inner slotted tube 194 and the outer slotted tube 110 to form the "tri-star" shape shown in FIG. 22B. The valve 30 may then be deployed by retracting both the inner slotted tube 194 and the outer slotted tube 110 relative to the valve 30, thereby allowing the valve to expand to its deployed state.

Figure 23A:
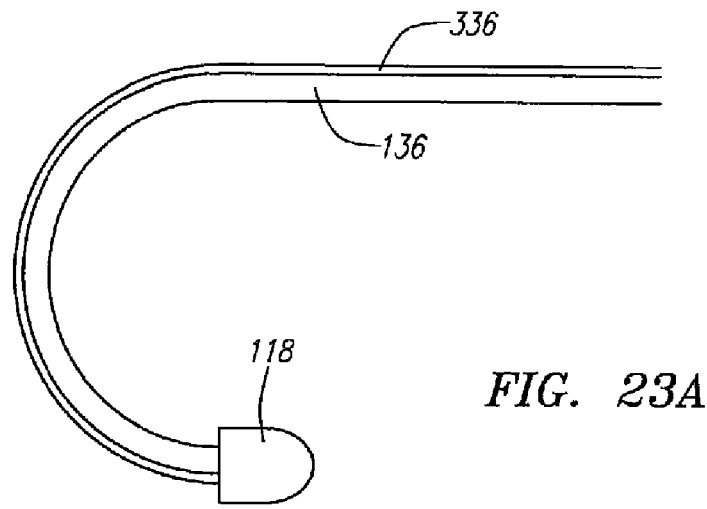
FIG. 23A is an illustration of a shape set nosecone shaft.
Figure 23B:
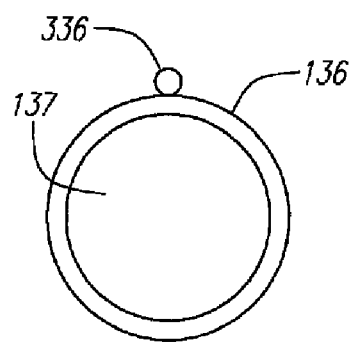
FIG. 23B is a cross-sectional end view of the shape set nosecone shaft of FIG. 23A.
Figure 23C:
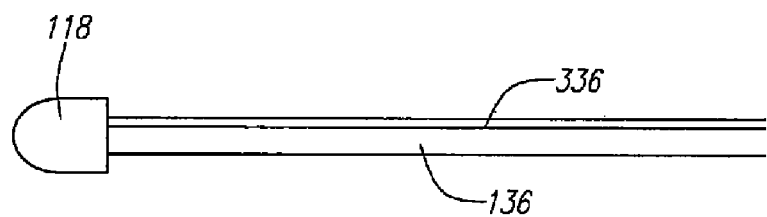
FIG. 23C is a side view of the shape set nosecone shaft of FIG. 23A showing the tensioning member in tension.

FIGS. 23A-C illustrate an optional shape set nosecone shaft 136. The shape set nosecone shaft 136 includes a pre-set shape formed into the distal end of the nosecone shaft 136 to facilitate the ability for the distal end of the delivery catheter 100 to pass over the aortic arch. This is particularly useful when the delivery catheter 100 is used for delivery of a prosthetic aortic valve. The shape set shown in FIG. 23A is generally in the form of a hook-shape, although other shapes is possible in order to improve the performance of the catheter. The shape set is also useful to stabilize the position of the catheter once it is delivered over the aortic arch. The shape set may be imparted by any mechanical or other method known to those skilled in the art. An optional tensioning member 336 may be provided on the external surface of the nosecone shaft 136. The tensioning member 336 is used to straighten the curvature of the shape set nosecone shaft 136 under the user's control. For example, as a tension force "T" is imparted to the tensioning member 336, such as by the user pulling proximally on the tensioning member 336 from the handle mechanism 102, the nosecone shaft 136 is straightened, as shown in FIG. 23C. The operation of the tensioning member 336 thereby provides the ability to manipulate the distal end of the delivery catheter 100 in a manner that provides an ability for the user to effectively steer the catheter over difficult or tortuous portions of the patient's vasculature. Other uses of the tensioning member 336 are described elsewhere herein.

C. Active Deployment of Undeployed and Not-Fully Deployed Valves

Although typically a prosthetic valve 30 such as those illustrated and described above in relation to FIGS. 1A-C—and those described in the '126 application and elsewhere—will fully deploy once it is released from the delivery catheter, it sometimes occurs that the valve does not deploy, or does not fully deploy. In most of these circumstances, the failure to deploy or to fully deploy is due to the fact that one or more panels 36 of a multi-panel valve 30 fails to change from its inverted state to its expanded state. One such example is illustrated in FIG. 24B, in which two panels 36 of a three-panel prosthetic valve 30 have expanded, but the upper panel 36 remains in a partially inverted state. Several mechanisms and methods for actively correcting these undeployed and not-fully deployed valves are described herein.

Several of the described mechanisms take advantage of the fact that, in most circumstances of non-full deployment, only a point contact is needed to cause the valve to fully expand. Accordingly, it may not be necessary to fully occlude the vessel in order to cause the valve or similar prosthetic device to fully expand. Thus, in most of the mechanisms and methods described, fluid flow or perfusion is still allowed through the valve and vessel as the active deployment procedure takes place. This is to be distinguished from the deployment methods applicable to most stent-like prosthetic devices in which fibrillation is induced to decrease flow during the deployment procedure. No such fibrillation is required for delivery and deployment of the prosthetic valves and similar devices described herein, nor for the active deployment mechanisms and methods described.

Figure 24A:
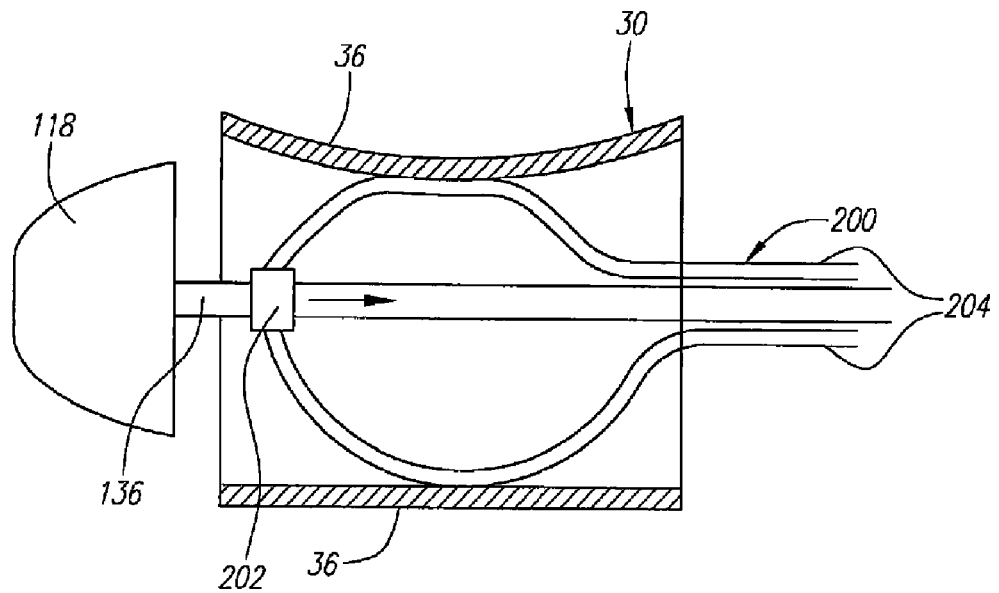
FIGS. 24A-C illustrate a side view in partial cross-section and two end views, respectively, of an active deployment mechanism for deploying a valve, in accordance with the present invention.
Figure 24B:
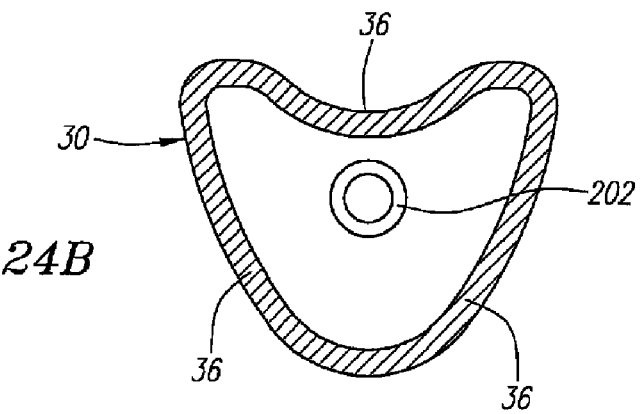
Figure 24C:
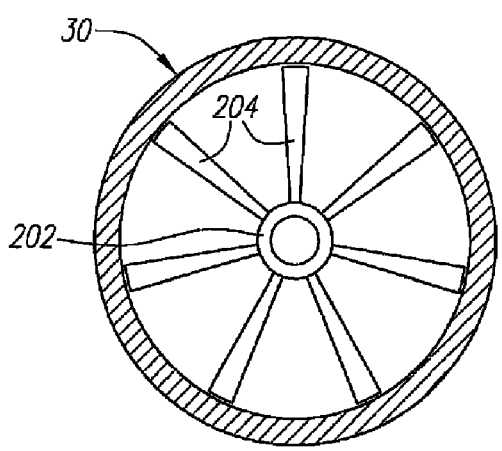

Turning to FIGS. 24A-C, a first such mechanism 200 includes a collar 202 and a plurality of wire forms 204 extending proximally from the collar 202. The mechanism 200 is intended to ride closely along the nosecone shaft 136 on any of the embodiments of the delivery catheter 100 described herein. As the mechanism 200 is advanced distally, it will enter and pass through the body of the partially-expanded valve 30. Once it is located there, the collar 202 may be retracted proximally, as shown by the arrow "A" in FIG. 24A, thereby causing the wire forms 204 to bow radially outward, (see, e.g., FIGS. 24A and 24C), engaging any inverted panels 36 of the valve 30 and causing them to expand to the fully expanded state. Preferably, the collar 202 is retracted by a tether or other control member that is connected to the collar 202 and that extends proximally to the handle where it can be manipulated by the user. Once the valve 30 is fully expanded, the collar 202 is advanced distally to cause the wire forms 204 to return to their unbowed state. The mechanism 200 may then be retracted into the delivery catheter 100. In alternative embodiments, the collar 202 may be provided with threads that engage threads formed on the nosecone shaft 136. Any other engagement providing relative movement between the collar 202 and the nosecone shaft 136 is also suitable.

As an alternative to the wire forms 204 shown in the above embodiment, a continuous segment of metallic or polymeric material having sufficient elasticity to expand and contract in the manner shown may be used. Other alternatives including using only a single band or material, or two, three, or more bands. Other alternative constructions and materials capable of expanding and contracting in the involved space internal of the undeployed or partially deployed prosthetic valve 30 are also contemplated, and are suitable for use as the active deployment mechanism 200 described herein.

Figure 25A:
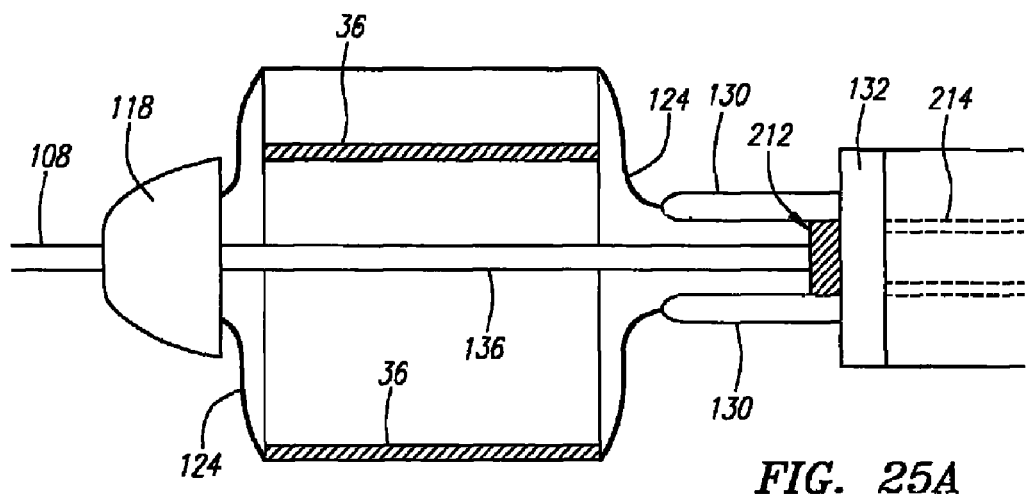
FIGS. 25A-C illustrate side views in partial cross-section of another active deployment mechanism for deploying a valve, in accordance with the present invention.
Figure 25B:
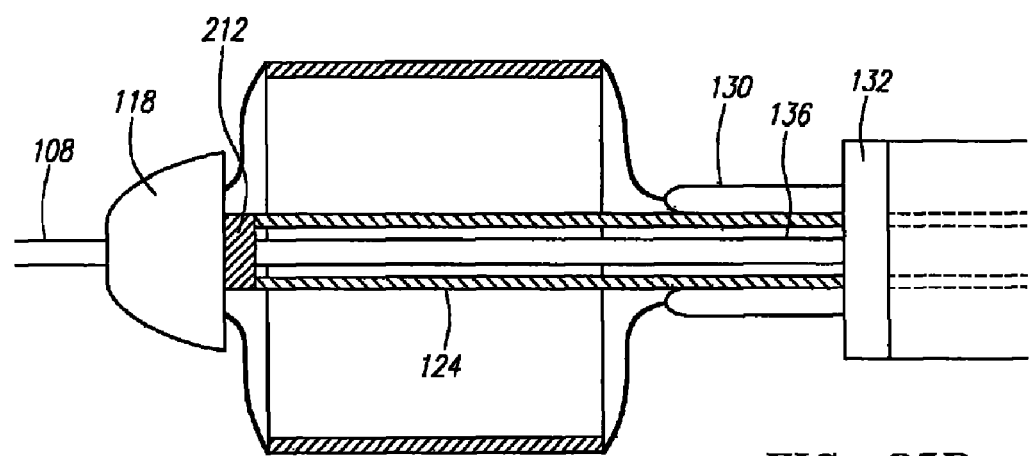
Figure 25C:
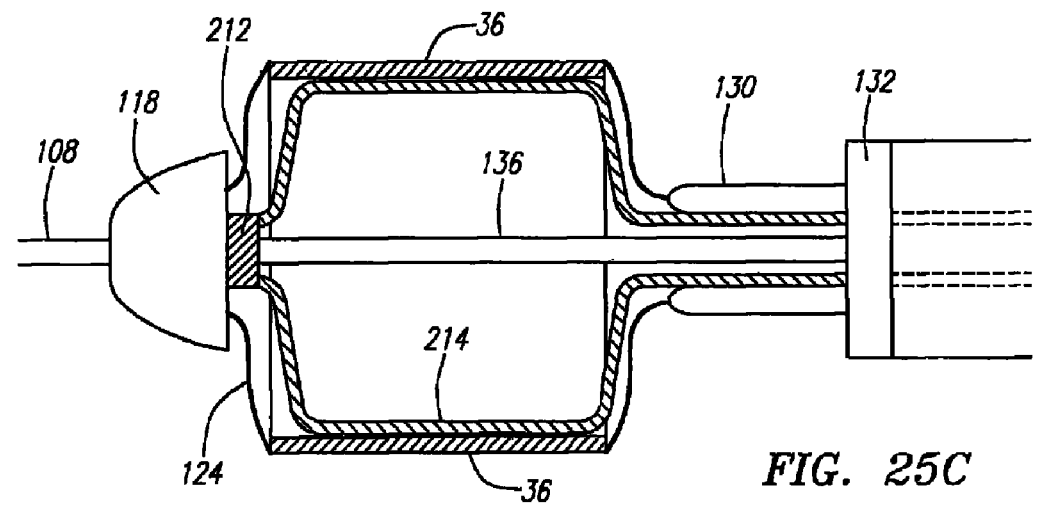

Another alternative construction for the active deployment mechanism is illustrated in FIGS. 25A-C. A partially deployed valve 30 includes an upper panel 36 that has not yet fully deployed. The deployment mechanism 200 comprises a collar 212 and a plurality of wire forms 214 extending proximally from the collar 212. Prior to use, the collar 212 is located internally of the catheter shaft 106 along the nosecone shaft 136, and the wire forms 214 lie flat along the nosecone shaft 136 proximally to the collar 212. (See FIG. 25A). The collar 212 is advanced distally through the partially deployed valve 30 until the collar 212 engages the proximal side of the nosecone 118, where further distal advancement is stopped. (See FIG. 25B). As additional distal-oriented force is applied to the mechanism 200, the wire forms 214 are caused to bow radially outward within the valve 30 to cause the upper panel 36 to fully deploy, as shown in FIG. 25C. The mechanism 200 is then collapsed and retracted proximally.

Turning to FIGS. 26A-E, several alternative balloon-based active deployment mechanism are described. The balloon-based systems include use of a balloon or other expandable member to cause an otherwise non-fully deployed valve 30 to expand to its fully expanded state upon deployment. Preferably, each of the balloons described herein includes an inflation lumen that is communicatively connected to the handle mechanism 102 or otherwise provided with a mechanism for selectively inflating the balloon(s) as needed.

Figure 26A:
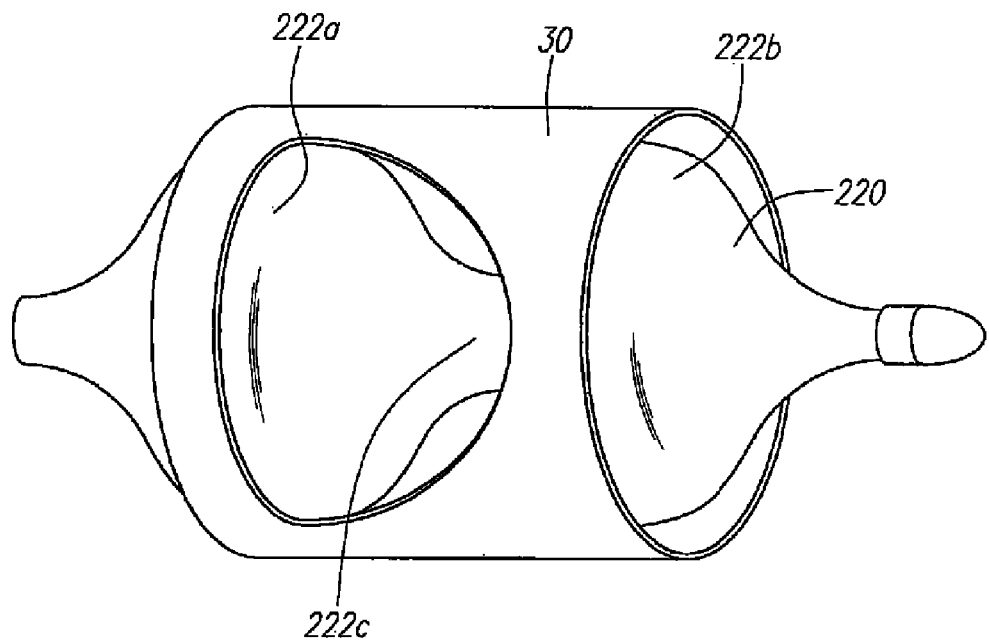
FIGS. 26A-E illustrate several embodiments of active deployment mechanism employing inflatable members, such as balloons.
Figure 26B:
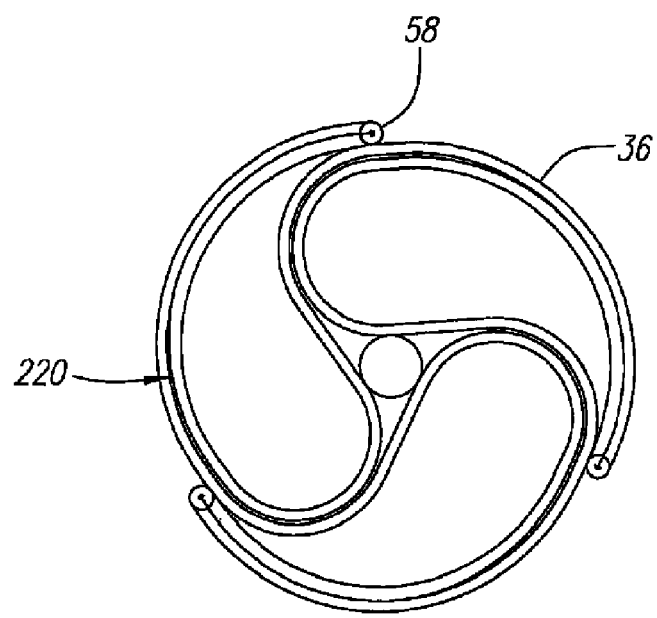

FIG. 26A illustrates a first embodiment in which a balloon 220 is provided internally of a prosthetic valve 30. The balloon 220 includes a pair of broad portions 222a that correspond with the proximal and distal ends of the valve 30, and a narrowed waist portion 222b that corresponds with the middle portion of the valve 30. The balloon 220 may optionally be provided in a fixed relationship with the valve body, as illustrated in FIG. 26B, wherein the balloon 220 is packaged with the valve 30 as the valve 30 is loaded into the delivery catheter and delivered to a treatment location. Thus, if the valve 30 is found not to have fully expanded after deployment, the balloon 220 may be inflated to cause full deployment.

Figure 26C:
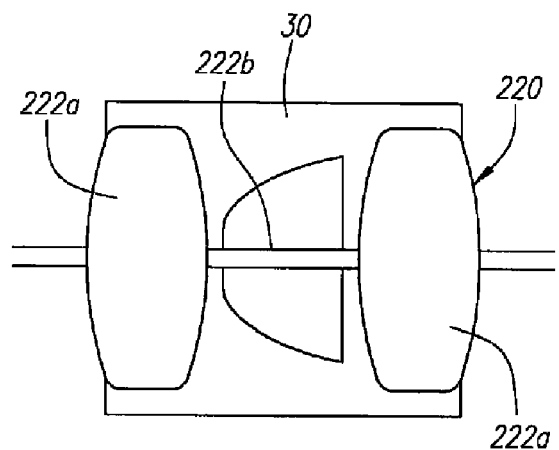
Figure 26D:
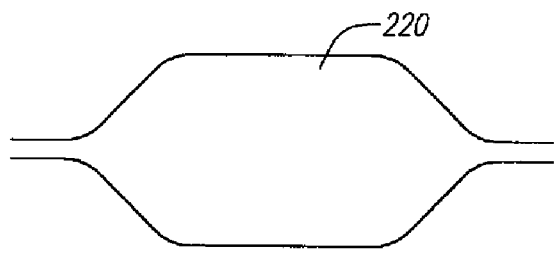
Figure 26E:
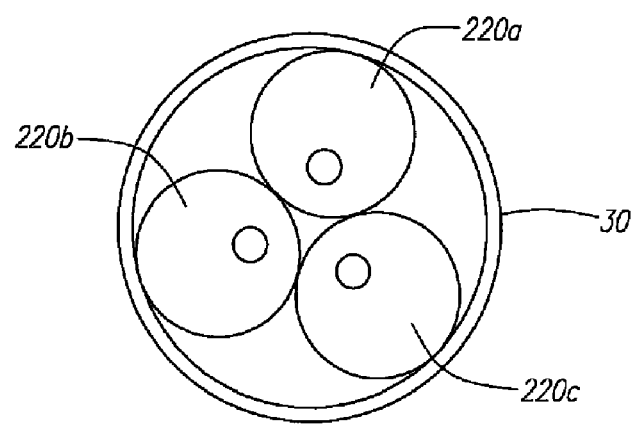

A number of optional balloon shapes and sizes are illustrated in FIGS. 26C-E. For example, in FIG. 26C, a single balloon 220 is shown having two large diameter portions 222a and a narrow, or smaller diameter portion 222b connecting the other two portions. In FIG. 26D, a single balloon 220 is shown, and would preferably extend through the entire length of the valve 30. In FIG. 26E, three separate balloons 220a-c are illustrated in an offset-tangent arrangement. The offset-tangent arrangement provides a number of benefits, including the ability to selectively inflate only one or more of the balloons 220a-c depending upon which valve panel 36 requires expansion. Also, the offset-tangent arrangement removes the need to fully occlude the vessel, thereby allowing fluid to flow around the balloon structure.

Figure 27A:
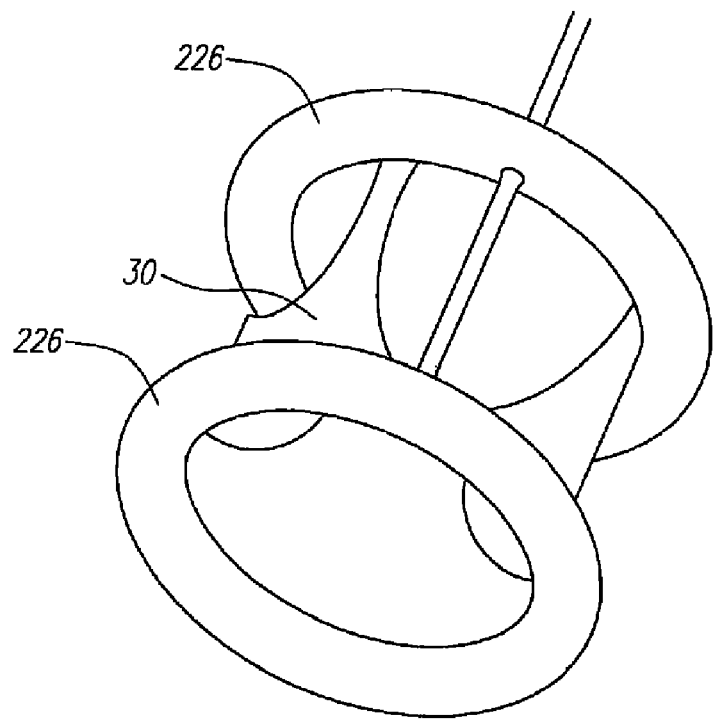
FIGS. 27A-B illustrates another embodiment of an active deployment mechanism employing inflatable members, such as balloons.
Figure 27B:
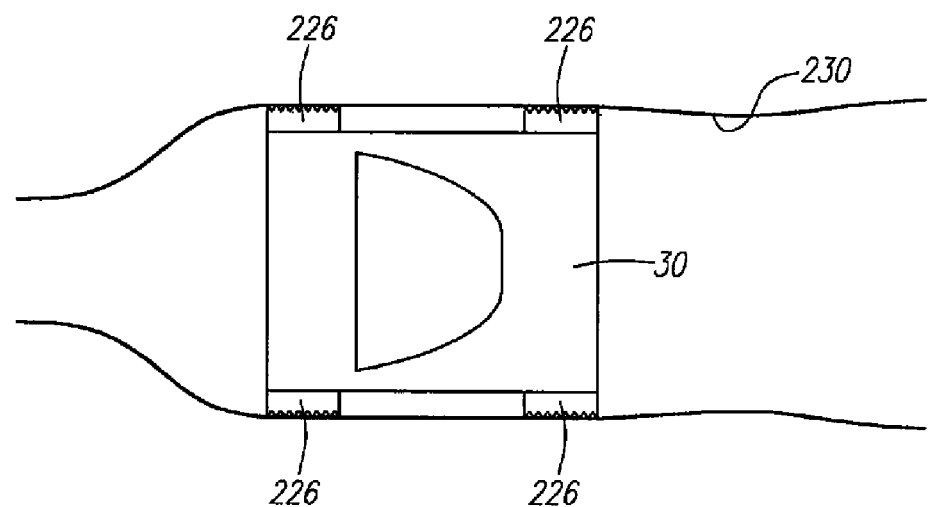

Turning to FIGS. 27A-B, in another alternative arrangement, a pair of toroidal balloons 226 are attached to the external surface of a prosthetic valve 30 near its proximal and distal ends, respectively. The pair of toroidal balloons 226 may be selectively expandable in order to actively deploy an otherwise non-fully deployed prosthetic valve 30. Upon expansion of the valve, the balloons 226 may then be deflated and left in place to serve as a seal against the vessel wall 230, as shown in FIG. 27B. Alternatively, the toroidal balloons 226 may be attached to the internal wall of the prosthetic valve 30, and may then be selectively detached from the valve 30 after the valve has been fully deployed.

Figure 28:
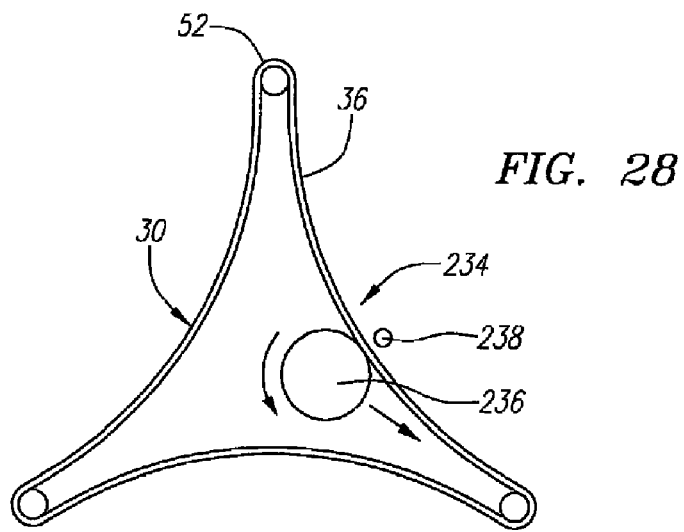
FIG. 28 illustrates an active deployment mechanism utilizing a roller and pincher.

FIG. 28 illustrates another active deployment mechanism 234 that includes a roller member 236 and a pincher member 238, each of which may be included on the distal end of a shaft that may be included with, or separate from, the delivery catheter 100. The roller 236 and pincher 238 advance along a panel 36 until the components encounter a hinge 52. Because of the diameter of the roller 236 relative to the hinge 52, when the roller 236 and pincher 238 engage the hinge 52, they force the hinge 52 to open, thereby causing the valve panel 36 to fully deploy.

Figure 29A:
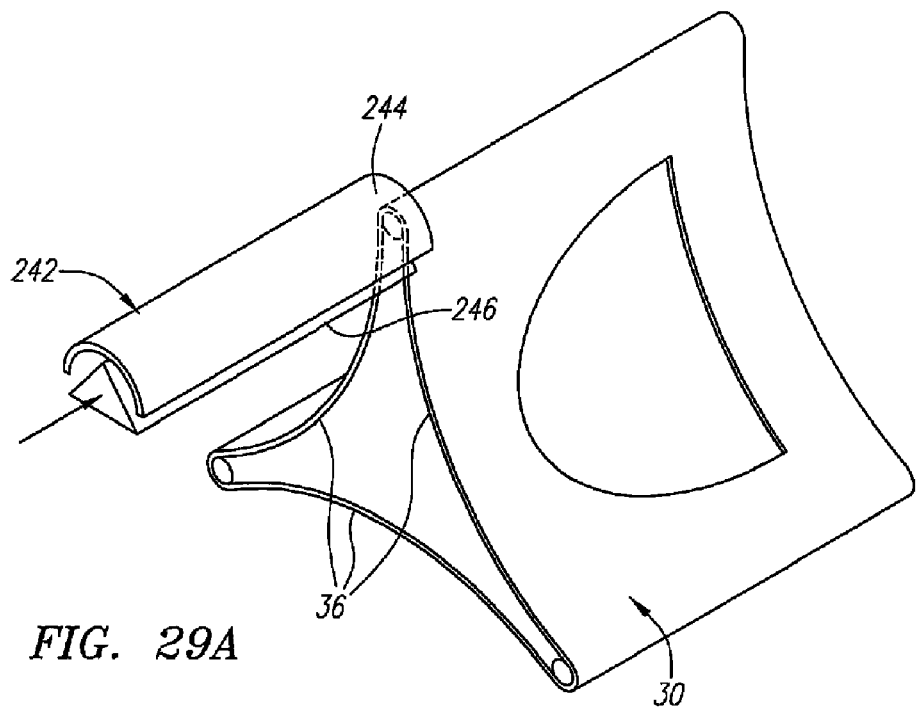
FIGS. 29A-B illustrate an active deployment mechanism utilizing a wedge.
Figure 29B:
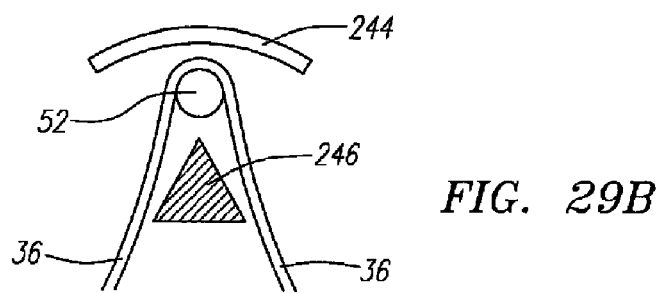

FIGS. 29A-B illustrate yet another deployment mechanism 242 that includes a wedge-shaped member having an upper guide 244 and a lower separator 246. As with the previous deployment mechanism 234, the present embodiment 242 be included on the distal end of a shaft that may be included with, or separate from, the delivery catheter 100. The wedge mechanism 242 is intended to be guided onto each of the hinges 52 of the undeployed or not-fully deployed valve 30. Because of the relative size and shape of the separator 246 portion of the wedge, the separator 246 causes the hinges 52 to open, thereby causing the valve panels 36 to expand to the fully deployed state.

Figure 30:
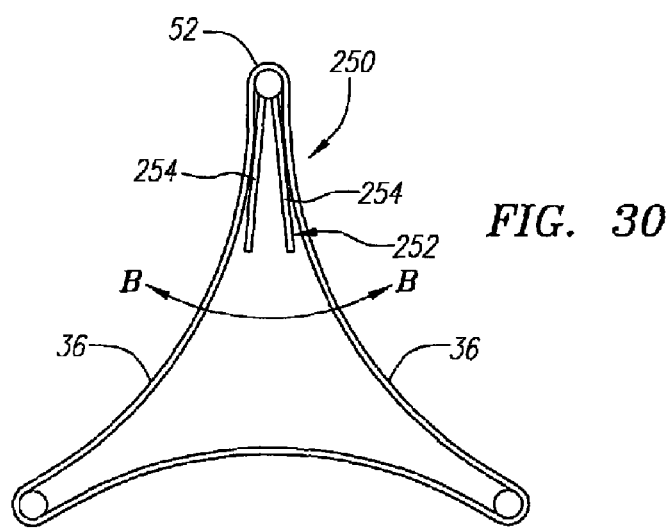
FIG. 30 illustrates an active deployment mechanism utilizing a torsion spring.

Turning next to FIG. 30, another deployment mechanism 250 includes a torsion spring 252 mounted to the internal surface of the valve 30. The torsion spring 252 may be integrated into and/or may form part of the hinge 52 of the valve 30, but is provided with a pair of arms 254 that extend into the interior of the valve 30, and which are biased to force the valve panels 36 radially outward to fully deploy the valve 30. The torsion spring 252 may be formed integrally with the valve 30, in which case it remains in place after valve deployment.

Figure 31A:
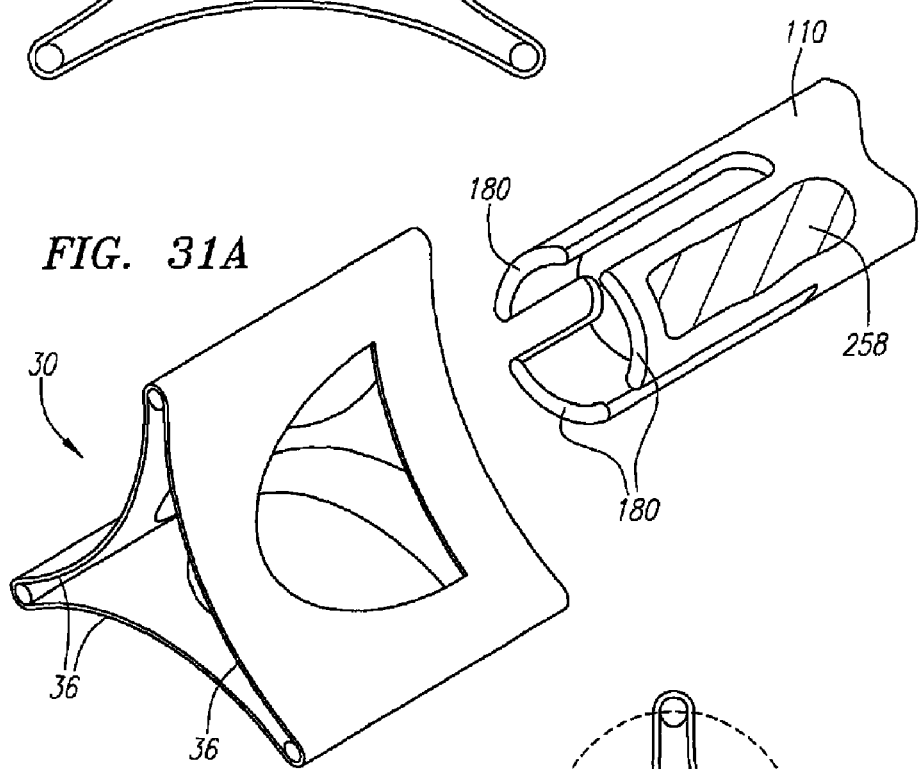
FIGS. 31A-B illustrate an active deployment mechanism utilizing a membrane balloon mounted on a slotted tube.
Figure 31B:
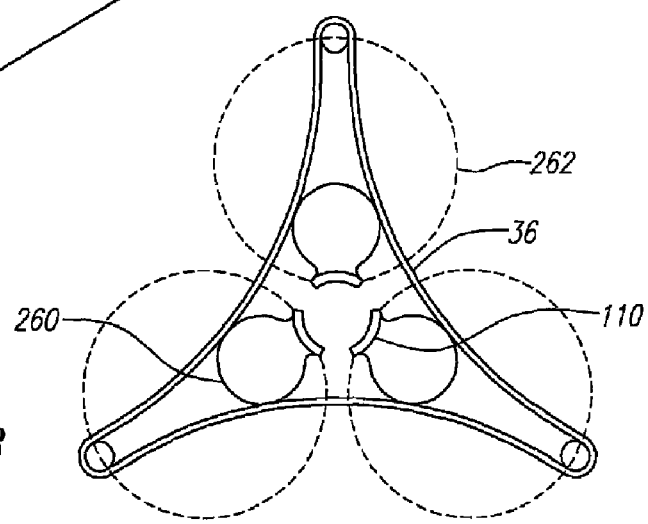

Turning to FIGS. 31A-B, yet another active valve deployment mechanism 256 includes a membrane balloon 258 formed on or attached to the external surface of each of the longitudinal members 180 of the slotted tube 110. The membrane balloons 258 are selectively and independently inflatable, as needed to actively deploy one or more undeployed panels of a prosthetic valve 30. As shown in FIG. 31A, the slotted tube 110 is first inserted into the valve 30, then one or more of the membrane balloons 258 is expanded. The expansion is initially to a first state 260 in which the membrane balloon engages the valve body panels 36, then, ultimately, to a second state 262 corresponding with full valve deployment. After deployment, the balloon may be deflated and the device removed from the patient's vasculature.

Figure 32:
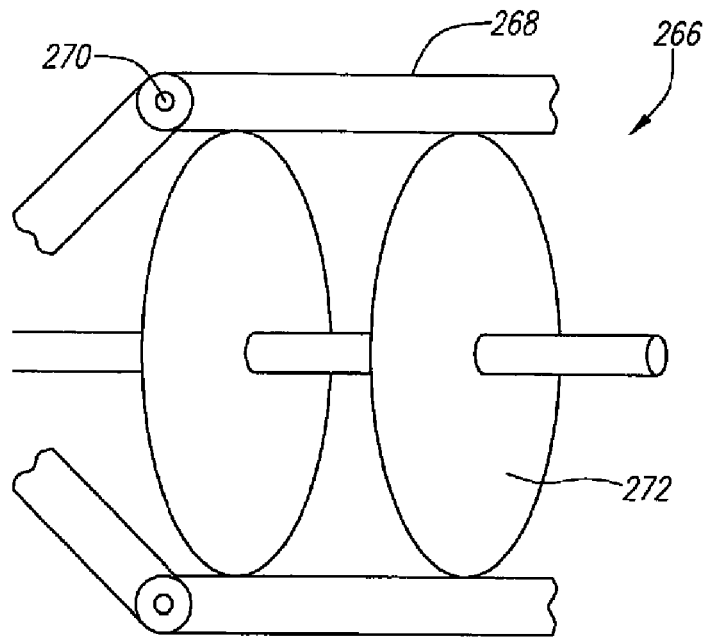
FIG. 32 illustrates an active deployment mechanism utilizing a plurality of linkages able to be expanded by an inflatable member.

Turning to FIG. 32, a still further alternative active valve deployment mechanism 266 includes a plurality of (preferably three) linkage members 268, each including a pivot 270 allowing the linkage member to expand radially, such as under the expansion force of an internal balloon 272 or other expandable member. Thus, as the deployment mechanism 266 is inserted into the undeployed prosthetic valve 30, it is able to be expanded by expanding or inflating the balloon 272.

Figure 33A:
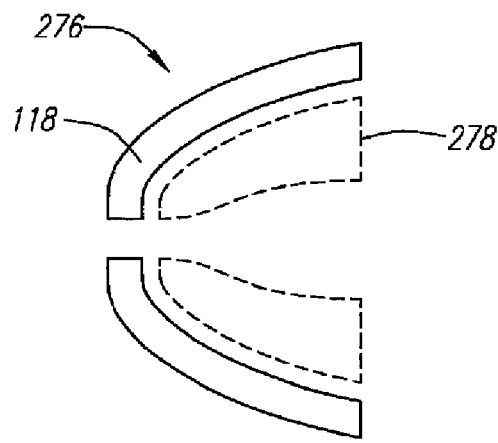
FIGS. 33A-B illustrate an active deployment mechanism utilizing an expansion balloon mounted within the nosecone of a delivery catheter.
Figure 33B:
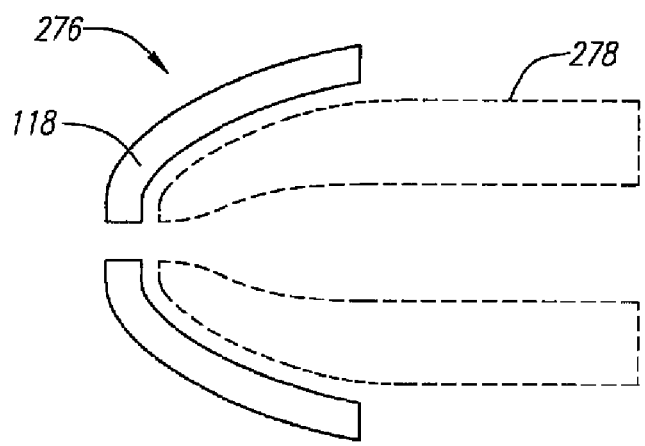

FIGS. 33A-B illustrate another active deployment mechanism 276 that incorporates a balloon 278 or other expandable member that is formed within the internal volume of the nosecone 118. In its undeployed state, shown in FIG. 33A, the balloon 278 does not extend past the distal end of the nosecone 118. However, if needed to expand the undeployed or not-fully deployed valve 30, the balloon 278 is expanded, as shown in FIG. 33B, thereby expanding the valve 30 to its expanded state.

Figure 34A:
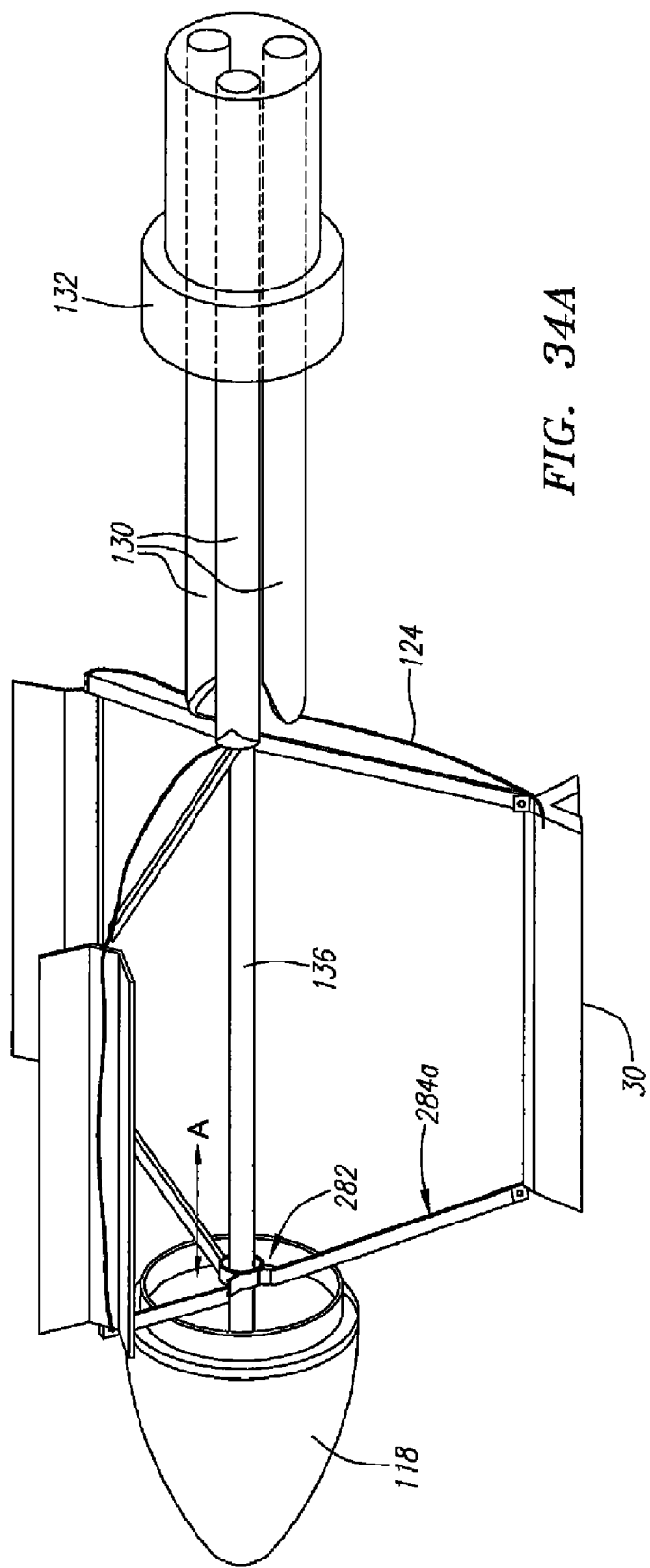
FIGS. 34A-C illustrate an active deployment mechanism utilizing a yoke and linkage system adapted to extend radially outward upon actuation.
Figure 34B:
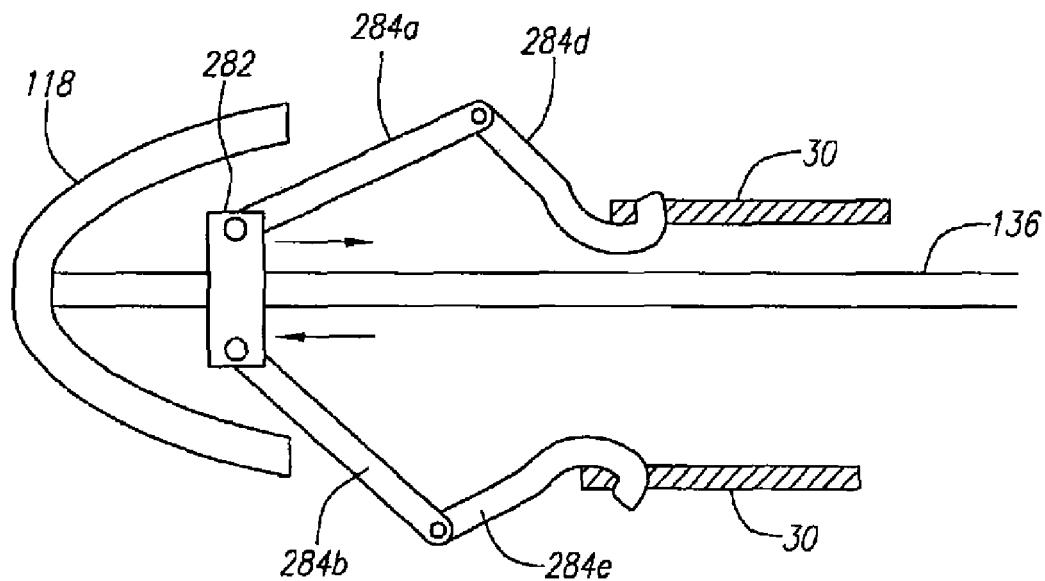
Figure 34C:
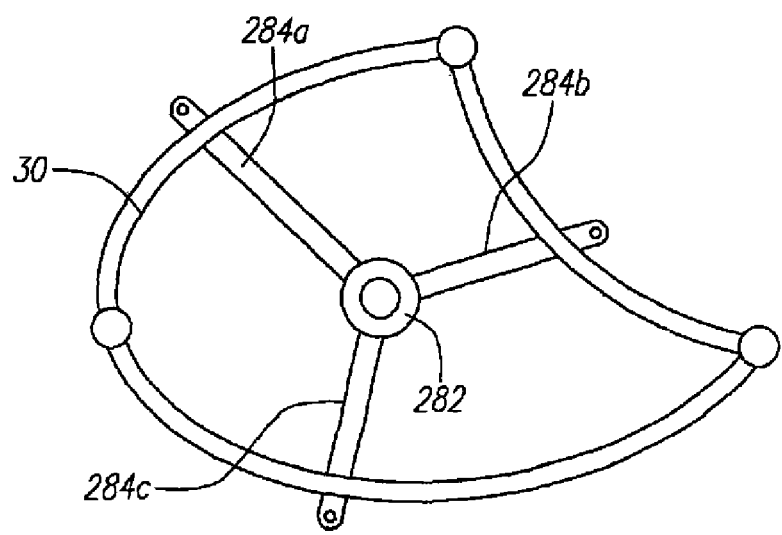

FIGS. 34A-C illustrate an active deployment mechanism that includes a yoke 282 that is slidably engaged over the nosecone shaft 136. A set of rotating linkages 284a-f are connected to the sliding yoke 282 such that, when the yoke 282 slides proximally along the nosecone shaft 136, as shown by the arrows "A" in FIG. 34A, the linkages 284a-f extend radially outward from the shaft 136. In the preferred embodiment, the free ends 284d-f of each of the linkages 284a-f are selectively attached to a respective panel of the valve 30 by a temporary mechanism. For example, the free ends 284d-f of the linkages may be attached to the valve panels by the tethers 124, such that when the tethers 124 are retracted, the valve panels are released from the linkages 284a-f. The nosecone 118 is preferably hollow to accommodate the mechanism prior to deployment.

Another optional active deployment mechanism utilizes the shape set nosecone shaft 136 and tensioning member 336 shown in FIGS. 23A-C. In the case of a valve 30 that does not fully deploy, it may be possible to manipulate the tensioning member 336 to cause either the nosecone 118, the nosecone shaft 136, or some other portion of the deployment mechanism 104 to engage the undeployed portion of the valve sufficiently to cause it to fully deploy. In a particularly preferred method, the tethers 124 associated with all of the fully deployed panels are allowed to remain slack, while the tether 124 associated with the undeployed panel is pulled taut to apply tension to the tether. By doing so, the nosecone 118 and the respective wrapping pin 130 are pulled to the respective distal and proximal edges of the valve panel, creating a relatively rigid linkage between the components. Once this is done, the tensioning member 336 (or other suitable steering mechanism) is actuated in order to cause the relatively rigid linkage to bias the still-inverted panel radially outward to the expanded position. This process may be repeated for each panel that is not fully expanded.

Finally, another alternative active deployment mechanism is to pressurize the aorta (or other treatment vessel) to cause the tissue defining the vessel to expand, thereby providing an adequate (increased) volume within which the valve 30 or other device is able to expand to its fully expanded state. Pressurization of the aorta (or other vessel) may be obtained by simply occluding the vessel, or by actively pressuring the vessel using an external source.

The preferred embodiments of the inventions that are the subject of this application are described above in detail for the purpose of setting forth a complete disclosure and for the sake of explanation and clarity. Those skilled in the art will envision other modifications within the scope and spirit of the present disclosure. Such alternatives, additions, modifications, and improvements may be made without departing from the scope of the present inventions, which is defined by the claims.

What is claimed is:

1. A method for deploying a prosthetic heart valve, comprising:
   advancing a prosthetic heart valve through vasculature of a patient to a treatment site along a wall of a blood vessel, the prosthetic heart valve comprising (i) a tubular support structure comprising a plurality of expandable segments oriented along a periphery of the support structure, and (ii) a plurality of valve leaflets coupled with the plurality of segments, wherein each expandable segment is transformable between a first shape and a second, expanded shape, and wherein at least one expandable segment is restrained in the first shape by a restraining member;
   removal of the restraining member from the at least one expandable segment such that the at least one expandable segment is free to spontaneously expand; and
   after removal of the restraining member, expanding an expandable deployment mechanism a first amount of distance against the at least one expandable segment in the first shape to cause the at least one expandable segment to expand a second amount of distance from the first shape to the second, expanded shape in contact with the vessel, wherein the first amount of distance is shorter than the second amount of distance and the expanding of the expandable deployment mechanism stops before the at least one expandable segment expands to the second, expanded shape in contact with the vessel.

2. The method of claim 1, wherein blood is free to flow through the expanded prosthetic heart valve when the expandable deployment mechanism is expanded therein.

3. The method of claim 1, wherein the expandable deployment mechanism initially contacts only a center region of the at least one expandable segment.

4. The method of claim 1, wherein the expandable deployment mechanism has an expanded diameter that is less than an expanded diameter of the tubular support structure.

5. The method of claim 4, wherein the expanded diameter of the expandable deployment mechanism is 16 millimeters and the expanded diameter of the tubular support structure is about 21 millimeters.

6. The method of claim 1, wherein the expandable deployment mechanism comprises a plurality of expandable elements and the at least one expandable segment is a first expandable segment, and wherein expanding the expandable deployment mechanism comprises expanding a first one of the plurality of expandable elements against the first expandable segment.

7. The method of claim 6, further comprising expanding a second one of the expandable elements against a second expandable segment after expanding the first one of the expandable elements.

8. The method of claim 6, wherein the expandable elements are each balloons.

9. The method of claim 6, wherein expanding the expandable deployment mechanism comprises expanding each of the plurality of expandable elements together.

10. The method of claim 6, wherein each of the expandable elements can be selectively expanded.

11. The method of claim 1, wherein the prosthetic heart valve is advanced through the vasculature by a delivery catheter that further comprises the expandable deployment mechanism.

12. The method of claim 1, wherein the prosthetic heart valve is advanced through the vasculature by a delivery catheter separate from a carrier that carries the expandable deployment mechanism.

13. The method of claim 1, wherein the plurality of expandable segments are configured to spontaneously expand, the method further comprising allowing the expandable segments to spontaneously expand prior to expanding the expandable deployment mechanism, wherein the at least one expandable segment does not spontaneously expand when allowed to do so.

14. The method of claim 13, wherein the expandable deployment mechanism comprises at least one balloon, and expanding the balloon causes the balloon to expand radially from a central axis of the tubular support structure.

15. A method for deploying a prosthetic heart valve, comprising:
 advancing a prosthetic heart valve through vasculature of a patient to a treatment site along a wall of a blood vessel, the prosthetic heart valve comprising (i) a tubular support structure comprising a plurality of expandable segments oriented along a periphery of the support structure, and (ii) a plurality of valve leaflets coupled with the plurality of segments, wherein each expandable segment is transformable between a first shape and a second, expanded shape, and wherein each expandable segment is restrained in the first shape by a restraining member;
 removal of the restraining member for each expandable segment such that each expandable segment is free to spontaneously expand; and
 expanding an expandable deployment mechanism a first amount of distance against the plurality of expandable segments in the first shape to cause the plurality of expandable segments to expand a second amount of distance from the first shape to the second, expanded shape in contact with the vessel, wherein the first amount of distance is shorter than the second amount of distance and the expanding of the expandable deployment mechanism stops before the plurality of expandable segments spontaneously expand to the second, expanded shape in contact with the vessel.

16. The method of claim 15, wherein the expandable deployment mechanism is a balloon coupled to an elongate member, the balloon configured to expand radially from about the periphery of the elongate member.

17. The method of claim 15, wherein the expandable deployment mechanism is a single balloon.

18. The method of claim 15, wherein blood is free to flow through the expanded prosthetic heart valve when the expandable deployment mechanism is expanded therein.

19. The method of claim 15, wherein the plurality of expandable segments are configured to spontaneously expand, the method further comprising allowing the expandable segments to spontaneously expand prior to expanding the expandable deployment mechanism, wherein the plurality of expandable segments do not spontaneously expand when allowed to do so.

* * * * *